(12) United States Patent
Hagadorn et al.

(10) Patent No.: US 8,674,040 B2
(45) Date of Patent: *Mar. 18, 2014

(54) PYRIDYLDIAMIDO TRANSITION METAL COMPLEXES, PRODUCTION AND USE THEREOF

(75) Inventors: John R. Hagadorn, Houston, TX (US); Renuka N. Ganesh, Houston, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/114,307

(22) Filed: May 24, 2011

(65) Prior Publication Data

US 2011/0224391 A1  Sep. 15, 2011

Related U.S. Application Data

(63) Continuation-in-part of application No. 12/180,132, filed on Jul. 25, 2008, now Pat. No. 7,973,116, and a continuation-in-part of application No. 13/071,738, filed on Mar. 25, 2011, which is a continuation-in-part of application No. 12/180,132, filed on Jul. 25, 2008.

(51) Int. Cl.
    *C08F 4/06* (2006.01)

(52) U.S. Cl.
    USPC .......................................................... 526/172

(58) Field of Classification Search
    USPC .......................................................... 526/172
    See application file for complete search history.

(56) References Cited

U.S. PATENT DOCUMENTS

| | | | |
|---|---|---|---|
| 5,318,935 A | 6/1994 | Canich et al. | |
| 6,103,657 A | 8/2000 | Murray | |
| 6,521,793 B1 | 2/2003 | Guram et al. | |
| 6,610,805 B1 | 8/2003 | Guram et al. | |
| 6,683,141 B1 * | 1/2004 | Gibson et al. | 526/161 |
| 6,750,345 B2 | 6/2004 | Boussie et al. | |
| 6,900,321 B2 | 5/2005 | Boussie et al. | |
| 7,018,949 B2 | 3/2006 | Boussie et al. | |
| 7,041,765 B2 | 5/2006 | Tau et al. | |
| 7,045,583 B2 | 5/2006 | Kuchta et al. | |
| 7,102,006 B2 | 9/2006 | Vogel et al. | |
| 7,164,020 B2 | 1/2007 | Vogel | |
| 7,425,661 B2 | 9/2008 | McConville et al. | |
| 7,973,116 B2 * | 7/2011 | Hagadorn et al. | 526/172 |
| 8,394,902 B2 * | 3/2013 | Hagadorn et al. | 526/172 |
| 2002/0156279 A1 | 10/2002 | Boussie et al. | |
| 2004/0220050 A1 | 11/2004 | Frazier et al. | |
| 2006/0135722 A1 | 6/2006 | Boussie et al. | |
| 2007/0191607 A1 | 8/2007 | Solan et al. | |
| 2010/0022726 A1 | 1/2010 | Hagadorn et al. | |
| 2011/0224391 A1 | 9/2011 | Hagadorn et al. | |
| 2011/0301310 A1 | 12/2011 | Hagadorn et al. | |

FOREIGN PATENT DOCUMENTS

| | | |
|---|---|---|
| JP | 2001-048925 | 2/2001 |
| WO | WO 2005/095469 | 10/2005 |
| WO | WO 2005095469 | * 11/2005 |
| WO | WO 2007/067965 | 6/2007 |
| WO | WO 2010-011435 | 1/2010 |
| WO | WO 2010/037059 | 4/2010 |

OTHER PUBLICATIONS

Froese et al., Mechanism of Activation of a Hafnium Pyridyl-Amide Olefin Polymerization Catalyst: Ligand Modification by Monomer, J. Am. Chem. Soc., 2007, vol. 129, No. 25, pp. 7831-7840.

Guérin et al., Synthesis, Structure, and Reactivity of Zirconium Alkyl Complexes Bearing Ancillary Pyridine Diamide Ligands, Organometallics, 1998, vol. 17, No. 23, pp. 5172-5177.

* cited by examiner

*Primary Examiner* — Yong Chu
*Assistant Examiner* — Sonya Wright
(74) *Attorney, Agent, or Firm* — Catherine L. Bell

(57) ABSTRACT

Pyridyldiamido transition metal complexes are disclosed for use in alkene polymerization to produce multimodal polyolefins.

29 Claims, 16 Drawing Sheets

Figure 1. 500 MHz $^1$H NMR spectrum of complex F dissolved in $CD_2Cl_2$

Figure 2. 500 MHz $^1$H NMR spectrum of complex I dissolved in $CD_2Cl_2$

Figure 3. 500 MHz $^1$H NMR spectrum of complex M dissolved in $CD_2Cl_2$

Figure 4. 500 MHz $^1$H NMR spectrum of complex R dissolved in $CD_2Cl_2$

Figure 5. 500 MHz $^1$H NMR spectrum of complex S dissolved in $CD_2Cl_2$

Figure 6. GPC data for run 1 of Table 2. (NOT PART OF INVENTION)
X-axis: Retention time (seconds); Y-axis: Absorbance Figure 7. GPC data for run 2 of Table 2. (NOT PART OF INVENTION)
X-axis: Retention time (seconds); Y-axis: Absorbance Figure 8. GPC data for run 3 of Table 2. (NOT PART OF INVENTION)
X-axis: Retention time (seconds); Y-axis: Absorbance Figure 9. GPC data for run 4 of Table 2. (NOT PART OF INVENTION)
X-axis: Retention time (seconds); Y-axis: Absorbance Figure 10. GPC data for run 5 of Table 2. (NOT PART OF INVENTION)
X-axis: Retention time (seconds); Y-axis: Absorbance Figure 11. GPC data for run 6 of Table 2. (NOT PART OF INVENTION)
X-axis: Retention time (seconds); Y-axis: Absorbance Figure 12. GPC data for run 7 of Table 2.

X-axis: Retention time (seconds); Y-axis: Absorbance

Figure 13. GPC data for run 8 of Table 2.
X-axis: Retention time (seconds); Y-axis: Absorbance Figure 14. GPC data for run 9 of Table 2.

X-axis: Retention time (seconds); Y-axis: Absorbance

Figure 15. GPC data for run 10 of Table 2.
X-axis: Retention time (seconds); Y-axis: Absorbance

PYRIDYLDIAMIDO TRANSITION METAL COMPLEXES, PRODUCTION AND USE THEREOF

US PRIORITY CLAIM

This application is a continuation-in part of U.S. Ser. No. 12/180,132, filed Jul. 25, 2008 now U.S. Pat. No. 7,973,116. This application is also a continuation-in part of U.S. Ser. No. 13/071,738, filed Mar. 25, 2011 which is a continuation-in part of U.S. Ser. No. 12/180,132, filed Jul. 25, 2008.

FIELD OF INVENTION

The invention relates to pyridyldiamido transition metal complexes and intermediates and processes for use in making such pyridyldiamido complexes. The transition metal complexes may be used as catalysts for alkene polymerization processes.

BACKGROUND OF INVENTION

Pyridyl amines have been used to prepare Group 4 complexes which are useful transition metal components in the polymerization of alkenes, see for example US 2002/0142912, U.S. Pat. No. 6,900,321, and U.S. Pat. No. 6,103,657, where the ligands have been used in complexes in which the ligands are coordinated in a bidentate fashion to the transition metal atom.

WO 2005/095469 shows catalyst compounds that use tridentate ligands through two nitrogen atoms (one amido and one pyridyl) and one oxygen atom.

US 2004/0220050A1 and WO 2007/067965 disclose complexes in which the ligand is coordinated in a tridentate fashion through two nitrogen (one amido and one pyridyl) and one carbon (aryl anion) donors.

A key step in the activation of these complexes is the insertion of an alkene into the metal-aryl bond of the catalyst precursor (Froese, R. D. J. et al., J. Am. Chem. Soc. 2007, 129, 7831-7840) to form an active catalyst that has both a five-membered and a seven-membered chelate ring.

WO 2010/037059 discloses pyridine containing amines for use in pharmaceutical applications.

There still is need for adding synthetic routes to widen the range of catalysts complexes that may be prepared and broaden their performance in alkene polymerization. The performance may be varied with respect to the amount of polymer produced per amount of catalyst (generally referred to as the "activity") under the prevailing polymerization conditions; the molecular weight and molecular weight distribution achieved at a given temperature; and the placement of higher alpha-olefins in terms of the degree of stereoregular placement.

SUMMARY OF INVENTION

This invention relates to novel transition metal complexes having tridentate NNN ligands. This invention also relates to pyridyldiamido and related transition metal complexes represented by the formula (A), (B), (I), or (II):

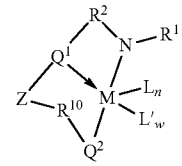

(A)

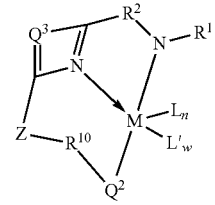

(B)

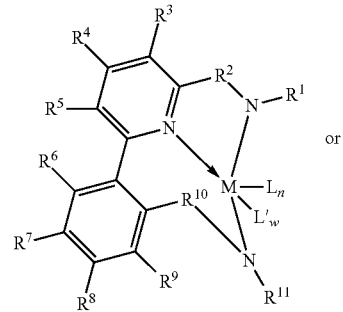

(I)

or

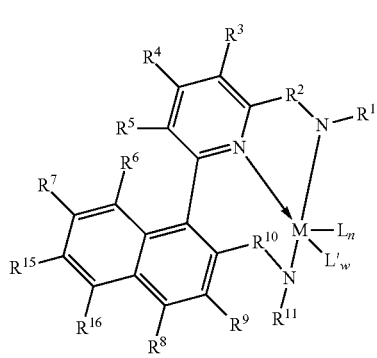

(II)

wherein:

M is a Group 3, 4, 5, 6, 7, 8, 9, 10, 11, or 12 metal;

$Q^1$ is a group that links $R^2$ and Z by a three atom bridge with the central of the three atoms being a group 15 or 16 element that preferably forms a dative bond to M;

$Q^2$ is a group that forms an anionic bond with M, including but not limited to a group 16 element (such as O or S) or $NR^{17}$ or $PR^{17}$, where $R^{17}$ is selected from hydrogen, hydrocarbyls, substituted hydrocarbyls, alkoxy, aryloxy, halogen, amino, and silyl;

$Q^3$ is -(TT)- or -(TTT)- (where each T is carbon or a heteroatom, preferably C, O, S, or N, and said carbon or heteroatom may be unsubstituted (e.g., hydrogen is bound to the carbon or heteroatom or substituted with one or more $R^{30}$ groups) that together with the "—C-$Q^3$=C—" fragment, forms a 5- or 6-membered cyclic group or a polycyclic group including the 5- or 6-membered cyclic group, where each $R^{30}$ group is, independently, hydrogen or a $C_1$ to $C_{100}$ hydrocarbyl group;

$R^1$ and $R^{11}$ are independently selected from the group consisting of hydrocarbyls, and substituted hydrocarbyls, or silyl groups;

$R^2$ and $R^{10}$ are each, independently, -$E(R^{12})(R^{13})$— with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

$R^3$, $R^4$, and $R^5$ are independently selected from the group consisting of hydrogen, hydrocarbyls, substituted hydrocarbyls, alkoxy, aryloxy, halogen, amino, and silyl, and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^6$, $R^7$, $R^8$, $R^9$, $R^{15}$, and $R^{16}$ are independently selected from the group consisting of hydrogen, hydrocarbyls, substituted hydrocarbyls, alkoxy, halogen, amino, and silyl, and wherein adjacent R groups ($R^6$ & $R^7$ and/or $R^7$ & $R^{15}$ and/or $R^{16}$ & $R^{15}$ and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings;

Z is —$(R_{14})_pC$—$C(R_{15})_q$—, where $R_{14}$ and $R_{15}$ are independently selected from the group consisting of hydrogen, hydrocarbyls, and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings;

p is 1 or 2;
q is 1 or 2;
L is an anionic leaving group, where the L groups may be the same or different and any two L groups may be linked to form a dianionic leaving group;
n is 0, 1, 2, 3, or 4;
L' is neutral Lewis base;
w is 0, 1, 2, 3, or 4; and
wherein n+w is no greater than 4;
provided that one of $R^2$ and $R^{10}$ is asymmetrically substituted and the other is symmetrically substituted.

This invention also relates to a process to make bimodal polyolefin using the catalysts described herein.

This invention further relates to process to make the above complex, process to make intermediates for the above complex and methods to polymerize olefins using the above complex.

DETAILED DESCRIPTION

Figure 1:
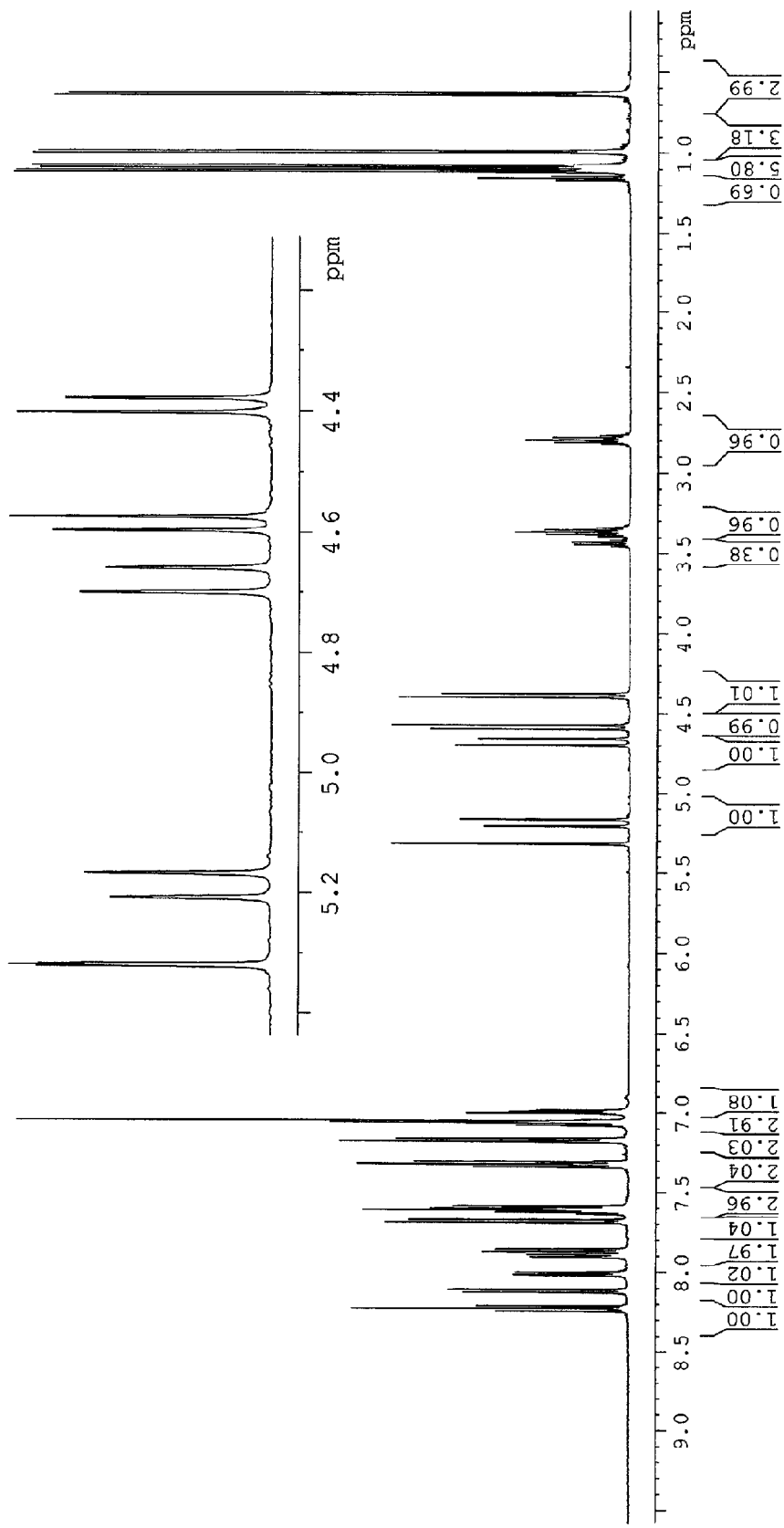
FIG. 1 is a 500 MHz $^1$H NMR spectrum of complex F dissolved in $CD_2Cl_2$.
Figure 2:
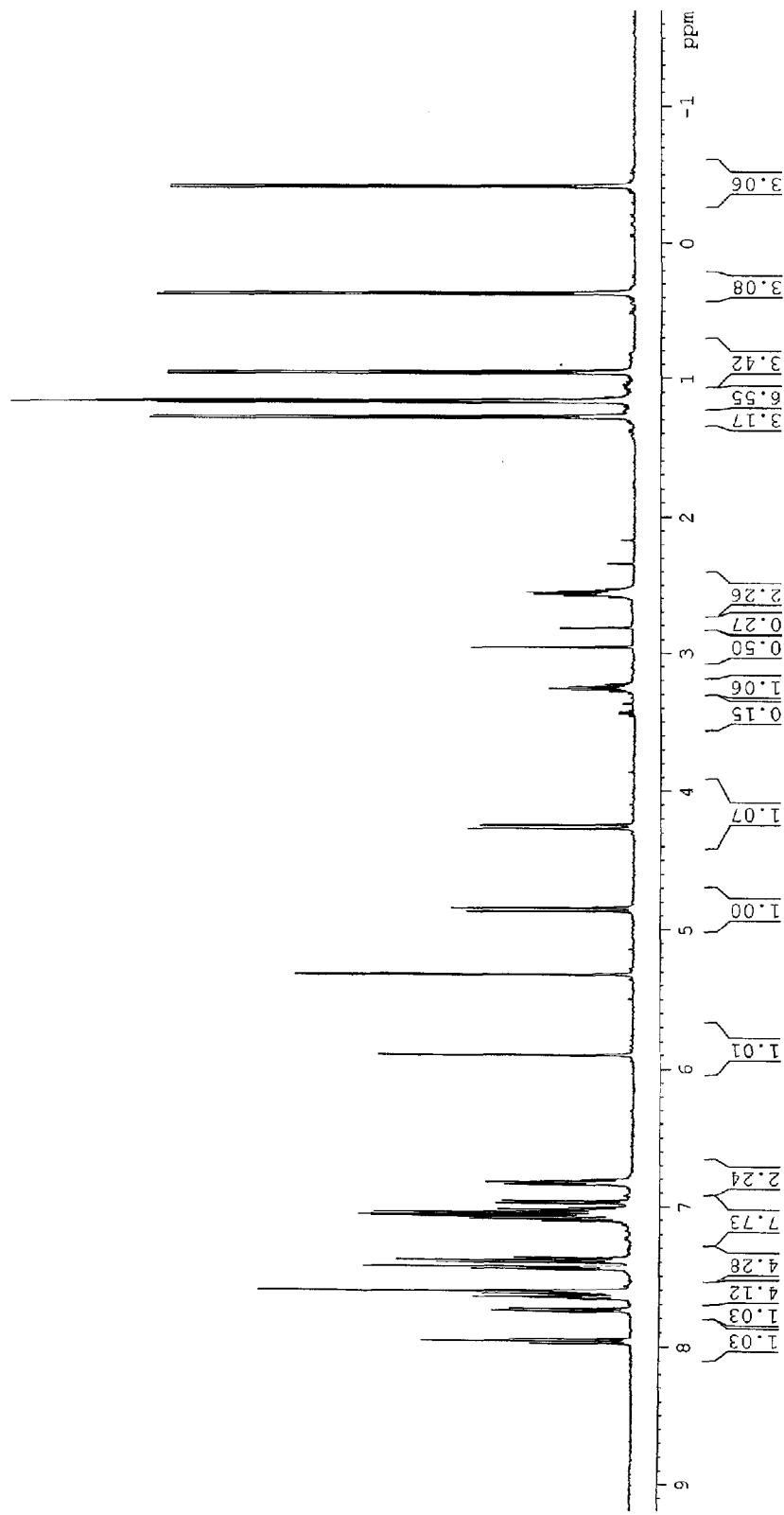
FIG. 2 is a 500 MHz $^1$H NMR spectrum of complex I dissolved in $CD_2Cl_2$.
Figure 3:
FIG. 3 is a 500 MHz $^1$H NMR spectrum of complex M dissolved in $CD_2Cl_2$.
Figure 4:
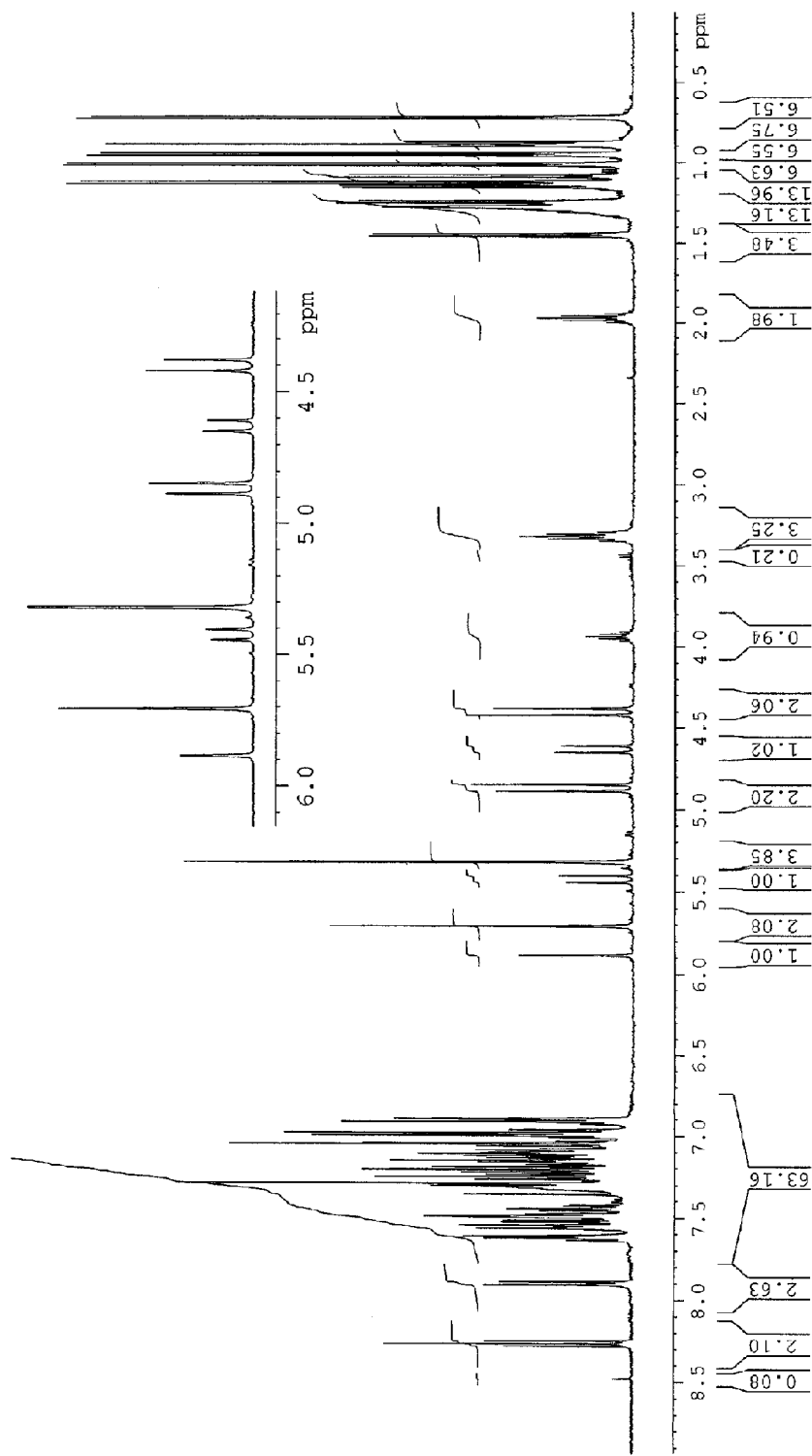
FIG. 4 is a 500 MHz $^1$H NMR spectrum of complex R dissolved in $CD_2Cl_2$.
Figure 5:
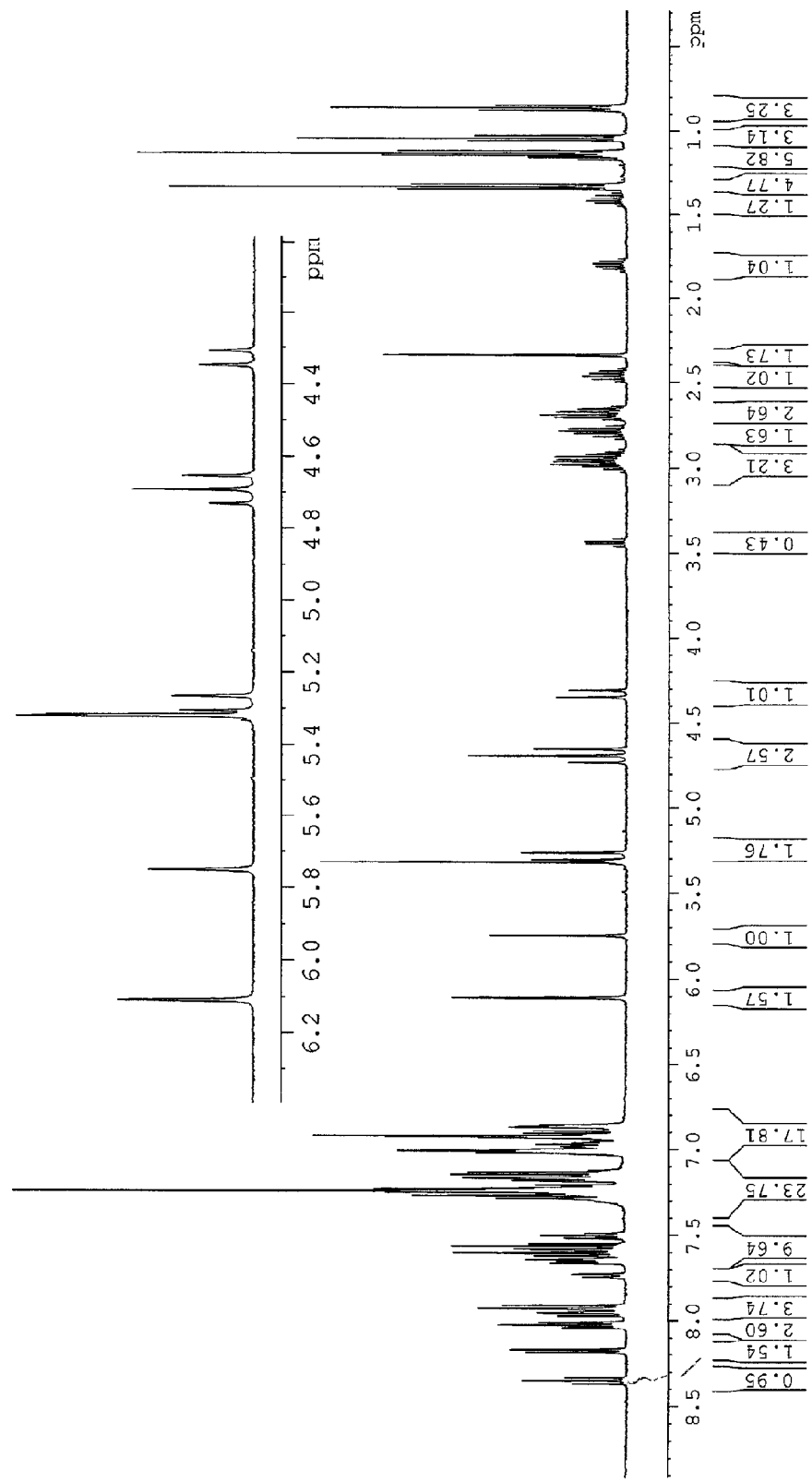
FIG. 5 is a 500 MHz $^1$H NMR spectrum of complex S dissolved in $CD_2Cl_2$.

The specification describes transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator which is believed to create a cation as a result of the removal of an anionic group, often referred to as a leaving group, from the transition metal.

As used herein, the numbering scheme for the Periodic Table groups is the new notation as set out in Chemical and Engineering News, 63(5), 27 (1985).

As used herein, Me is methyl, Et is ethyl, Bu is butyl, t-Bu and tBu are tertiary butyl, Pr is propyl, iPr and $^i$Pr are isopropyl, Cy is cyclohexyl, THF (also referred to as thf) is tetrahydrofuran, Bn is benzyl, and Ph is phenyl.

The term "substituted" generally means that a hydrogen of the substituted species has been replaced with a different atom or group of atoms. For example, methyl-cyclopentadiene is cyclopentadiene that has been substituted with a methyl group. Likewise, picric acid can be described as phenol that has been substituted with three nitro groups, or, alternatively, as benzene that has been substituted with one hydroxy and three nitro groups.

The terms "hydrocarbyl radical," "hydrocarbyl," and "hydrocarbyl group" are used interchangeably throughout this document. Likewise, the terms "group," "radical," and "substituent" are also used interchangeably in this document. For purposes of this disclosure, "hydrocarbyl radical" is defined to be $C_1$-$C_{100}$ radicals, that may be linear, branched, or cyclic, and when cyclic, aromatic or non-aromatic.

A substituted hydrocarbyl radical is a hydrocarbyl radical in which at least one hydrogen atom of the hydrocarbyl radical has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, $PbR^*_3$, and the like, or where at least one heteroatom has been inserted within a hydrocarbyl ring.

The term "catalyst system" is defined to mean a complex/activator pair. When "catalyst system" is used to describe such a pair before activation, it means the unactivated catalyst complex (precatalyst) together with an activator and, optionally, a co-activator. When it is used to describe such a pair after activation, it means the activated complex and the activator or other charge-balancing moiety. The transition metal compound may be neutral as in a precatalyst, or a charged species with a counter ion as in an activated catalyst system.

Complex, as used herein, is also often referred to as catalyst precursor, precatalyst, catalyst, catalyst compound, transition metal compound, or transition metal complex. These words are used interchangeably. Activator and cocatalyst are also used interchangeably.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments, a co-activator can be pre-mixed with the transition metal compound to form an alkylated transition metal compound.

Noncoordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

When a polymer or oligomer is referred to as comprising an olefin, the olefin present in the polymer or oligomer is the polymerized or oligomerized form of the olefin. An oligomer is defined to be compositions having 2-50 monomer units. A polymer is defined to be compositions having 51 or more monomer (mer) units.

A "polymer" has the same or different mer units. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically.

A higher α-olefin is defined to be an α-olefin having 4 or more carbon atoms.

Unless otherwise noted, all molecular weights units (e.g., Mw, Mn, Mz) are g/mol.

Unless otherwise noted all melting points ($T_m$) are DSC second melt.

A "ring carbon atom" is a carbon atom that is part of a cyclic ring structure. By this definition, a benzyl group has six ring carbon atoms and para-methylstyrene also has six ring carbon atoms.

The term "aryl" or "aryl group" means a six carbon aromatic ring and the substituted variants thereof, including but not limited to, phenyl, 2-methyl-phenyl, xylyl, 4-bromo-xylyl. Likewise heteroaryl means an aryl group where a ring carbon atom (or two or three ring carbon atoms) has been replaced with a heteroatom, preferably N, O, or S.

The term "ring atom" means an atom that is part of a cyclic ring structure. By this definition, a benzyl group has six ring atoms and tetrahydrofuran has 5 ring atoms.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom substituted ring.

As used herein the term "aromatic" also refers to pseudoaromatic heterocycles which are heterocyclic substituents that have similar properties and structures (nearly planar) to aromatic heterocyclic ligands, but are not by definition aromatic; likewise, the term aromatic also refers to substituted aromatics.

The term "continuous" means a system that operates without interruption or cessation. For example, a continuous process to produce a polymer would be one where the reactants are continually introduced into one or more reactors and polymer product is continually withdrawn.

A solution polymerization means a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva and J. C. Pinto, Ind. Eng, Chem. Res. 29, 2000, 4627.

A bulk polymerization means a polymerization process in which the monomers and/or comonomers being polymerized are used as a solvent or diluent using little or no inert solvent as a solvent or diluent. A small faction of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

The term "multimodal," when used to describe a polymer or polymer composition, means "multimodal molecular weight distribution," which is understood to mean that the Gel Permeation Chromatography (GPC) trace, plotted as Absorbance versus Retention Time (seconds), has more than one peak or inflection points. An "inflection point" is that point where the second derivative of the curve changes in sign (e.g., from negative to positive or vice versa). For example, a polyolefin composition that includes a first lower molecular weight polymer component (such as a polymer having an Mw of 100,000 g/mol) and a second higher molecular weight polymer component (such as a polymer having an Mw of 300,000 g/mol) is considered to be a "bimodal" polyolefin composition. Preferably the Mw's of the polymer or polymer composition differ by at least 10%, relative to each other, preferably by at least 20%, preferably at least 50%, preferably by at least 100%, preferably by a least 200%. Likewise, in a preferred embodiment, the Mw's of the polymer or polymer composition differ by 10% to 10,000%, relative to each other, preferably by 20% to 1000%, preferably 50% to 500%, preferably by at least 100% to 400%, preferably 200% to 300%.

"Catalyst activity" is a measure of how many grams of polymer (P) are produced using a polymerization catalyst comprising W mmol of transition metal (M), over a period of time of T hours; and may be expressed by the following formula: P/(T×W).

In a first aspect of the invention there is provided a pyridyl-diamido transition metal complex (optionally for use in alkene polymerization) represented by the formula (A) or (B):

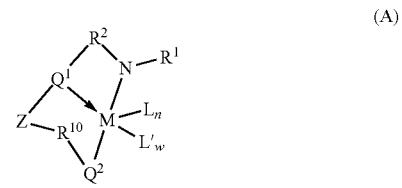

(A)

-continued

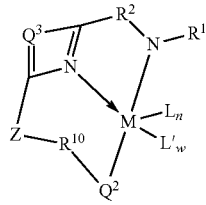

(B)

wherein:

M is a Group 3, 4, 5, 6, 7, 8, 9, 10, 11, or 12 metal;

$Q^1$ is a group that links $R^2$ and Z by a three atom bridge with the central of the three atoms being a group 15 or 16 element that preferably forms a dative bond to M, preferably represented by the formula: $-G^1-G^2-G^3-$ where $G^2$ is a group 15 or 16 atom (preferably N, S, P, or O, preferably N or P, preferably N), $G^1$ and $G^3$ are each a group 14, 15, or 16 atom, preferably C, Si, N, S, P, or O (preferably C), where $G^1$, $G^2$ and $G^3$, or $G^1$ and $G^2$, or $G^1$ and $G^3$, or $G^2$ and $G^3$ may form a singular or multi ring system, and if either of $G^1$ and/or $G^3$ is a group 14 atom (such as C or Si) then $R^{30}$ and $R^{31}$ are bound to such G atom(s), and if $G^1$, $G^2$, and/or $G^3$ is a group 15 atom (such as N or P) then $R^{30}$ is bound to such G atom(s), where each $R^{30}$ and $R^{31}$ is, independently, hydrogen or a $C_1$ to $C_{100}$ hydrocarbyl group (alternately a $C_1$ to $C_{40}$, alternately a $C_1$ to $C_{20}$ hydrocarbyl group);

$Q^2$ is a group that forms an anionic bond with M, including but not limited to a group 16 element (such as O or S) or $NR^{17}$ or $PR^{17}$, where $R^{17}$ is selected from hydrogen, hydrocarbyls, substituted hydrocarbyls, alkoxy, aryloxy, halogen, amino, and silyl;

$Q^3$ is -(TT)- or -(TTT)- (where each T is carbon or a heteroatom, preferably C, O, S, or N, and said carbon or heteroatom may be unsubstituted (e.g., hydrogen is bound to the carbon or heteroatom or substituted with one or more $R^{30}$ groups) that together with the "—C-$Q^3$=C—" fragment, forms a 5- or 6-membered cyclic group or a polycyclic group including the 5- or 6-membered cyclic group;

$R^1$ is selected from the group consisting of hydrocarbyls, and substituted hydrocarbyls, or silyl groups;

$R^2$ and $R^{10}$ are each, independently, $-E(R^{12})(R^{13})-$ with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

Z is $-(R_{14})_pC-C(R_{15})_q-$, where $R^{14}$ and $R^{15}$ are independently selected from the group consisting of hydrogen, hydrocarbyls, and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings;

p is 1 or 2;

q is 1 or 2;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3, or 4; and wherein n+w is no greater than 4;

provided that one of $R^2$ and $R^{10}$ is asymmetrically substituted and the other is symmetrically substituted.

Asymmetrically substituted is defined to mean that $R^{12}$ and $R^{13}$ are not the same.

Symmetrically substituted means that $R^{12}$ and $R^{13}$ are the same. For purposes of this definition, same does not necessarily mean having the same carbon number as n-butyl and isobutyl are defined as not the same.

In a preferred embodiment, $Q^1$ is a substituted or unsubstituted pyridine group linked to Z and $R^2$ through the carbons in the 2 and 6 position (of the pyridine ring, with the nitrogen being the 1 position).

In a preferred embodiment, $G^1$ and $G^3$ are each independently selected from C, N, O, and S, preferably $G^1$ and $G^3$ with their respective R groups are methyl, ethyl, propyl, butyl, pentyl, hexyl, octyl, and the like, preferably $G^1$ and $G^3$ with their respective R groups are formed into a ring structure, preferably pyridine.

In a preferred embodiment, $Q^2$ is $NR^{17}$, where $R^{17}$ is selected from hydrocarbyls (such as alkyls and aryls), substituted hydrocarbyls (such as heteroaryls), and silyl groups, preferably $R^{17}$ is a phenyl group or a substituted phenyl group, wherein when $R^{11}$ is substituted, $R^{11}$ is substituted with between one to five substituents that include F, Cl, Br, I, $CF_3$, $NO_2$, alkoxy, dialkylamino, aryl, and alkyl groups having 1 to 10 carbons, such as methyl, ethyl, propyl, butyl, pentyl, hexyl, heptyl, octyl, nonyl, decyl, and isomers thereof.

In a preferred embodiment, $Q^3$ is a three carbon linker (CH—CH—CH) that forms a pyridine ring. In another preferred embodiment, $Q^3$ is two atom linker containing one carbon and one group 15 or 16 element such that the linker forms a five-membered heterocycle, such as an imidazole or a substituted imidazole.

In another aspect of the invention there is provided a pyridyldiamido transition metal complex (optionally for use in alkene polymerization) represented by the formula (I) or (II):

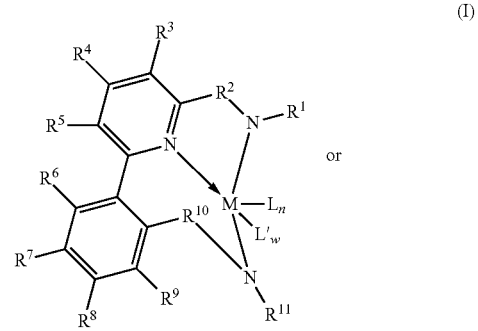

(I)

or

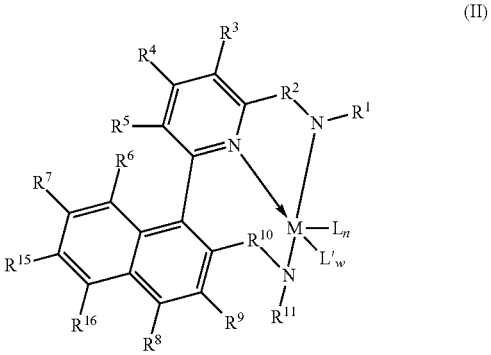

(II)

wherein:

M is a Group 3, 4, 5, 6, 7, 8, 9, 10, 11, or 12 metal;

$R^1$ and $R^{11}$ are independently selected from the group consisting of hydrocarbyls, and substituted hydrocarbyls, or silyl groups;

$R^2$ and $R^{10}$ are each, independently, -E($R^{12}$)($R^{13}$)— with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

$R^3$, $R^4$, and $R^5$ are independently selected from the group consisting of hydrogen, hydrocarbyls, substituted hydrocarbyls, alkoxy, aryloxy, halogen, amino, and silyl, and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^6$, $R^7$, $R^8$, $R^9$, $R^{15}$, and $R^{16}$ are independently selected from the group consisting of hydrogen, hydrocarbyls, substituted hydrocarbyls, alkoxy, halogen, amino, and silyl, and wherein adjacent R groups ($R^6$ & $R^7$, and/or $R^7$ & $R^{15}$, and/or $R^{16}$ & $R^{15}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3, or 4; and wherein n+w is not greater than 4;

provided that one of $R^2$ and $R^{10}$ is asymmetrically substituted and the other is symmetrically substituted.

Preferably, the R groups above and other R groups mentioned hereafter, contain from 1 to 30, preferably 2 to 20 carbon atoms, especially from 6 to 20 carbon atoms.

Preferably, M is Ti, Zr, or Hf, and/or E is carbon, with Zr or Hf based complexes being especially preferred.

In a preferred embodiment, $R^1$ and $R^{11}$ may be independently selected from phenyl groups that are variously substituted with between zero to five substituents that include F, Cl, Br, I, $CF_3$, $NO_2$, alkoxy, dialkylamino, aryl, and alkyl groups having 1 to 10 carbons, such as methyl, ethyl, propyl, butyl, pentyl, hexyl, heptyl, octyl, nonyl, decyl, and isomers thereof.

In a preferred embodiment, L may be selected from halide, alkyl, aryl, alkoxy, amido, hydrido, phenoxy, hydroxy, silyl, allyl, alkenyl, and alkynyl. The selection of the leaving groups depends on the synthesis route adopted for arriving at the complex and may be changed by additional reactions to suit the later activation method in polymerization. For example, a preferred L is alkyl when using non-coordinating anions such as N,N-dimethylanilinium tetrakis(pentafluorophenyl)-borate or tris(pentafluorophenyl)borane. In another embodiment, two L groups may be linked to form a dianionic leaving group, for example oxalate.

In another embodiment, each L' is independently selected from the group consisting of ethers, thio-ethers, amines, nitriles, imines, pyridines, and phosphines, preferably ethers.

Preferred $R^2$ groups and preferred $R^{10}$ groups include $CH_2$, $CMe_2$, $SiMe_2$, $SiEt_2$, $SiPr_2$, $SiBu_2$, $SiPh_2$, $Si(aryl)_2$, $Si(alkyl)_2$, CH(aryl), CH(Ph), CH(alkyl), and CH(2-isopropylphenyl).

Preferred pairing of $R^2$ and $R^{10}$ groups (expressed as $R^2$ & $R^{10}$ includes: ($CH_2$ & CH(Ph)), ($CMe_2$ and CH(Ph)), ($CH_2$ and CH(aryl)), ($CH_2$ and CH(alkyl)), where alkyl is a $C_1$ to $C_{40}$ alkyl group (preferably $C_1$ to $C_{20}$ alkyl, preferably one or more of methyl, ethyl, propyl, butyl, pentyl, hexyl, heptyl, octyl, nonyl, decyl, undecyl, dodecyl, and isomers thereof), aryl is a $C_5$ to $C_{40}$ aryl group (preferably a $C_6$ to $C_{20}$ aryl group, preferably phenyl or substituted phenyl, preferably phenyl, 2-isopropylphenyl, or 2-tertbutylphenyl).

In another embodiment, $R^2$ is $CH_2$ or $CMe_2$ and $R^{10}$ is selected from the group consisting of CH(Ph), CH(aryl), and CH(alkyl), where alkyl is a $C_1$ to $C_{40}$ alkyl group (preferably $C_1$ to $C_{20}$ alkyl, preferably one or more of methyl, ethyl, propyl, butyl, pentyl, hexyl, heptyl, octyl, nonyl, decyl, undecyl, dodecyl, and isomers thereof), aryl is a $C_5$ to $C_{40}$ aryl group (preferably a $C_6$ to $C_{20}$ aryl group, preferably phenyl or substituted phenyl, preferably phenyl, 2-isopropylphenyl, or 2-tertbutylphenyl).

In any embodiment described herein, E is preferably carbon.

In any embodiment described herein, $R^2$ is represented by the formula:

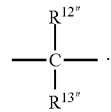

In any embodiment described herein, $R^{12''}$ is hydrogen, alkyl, aryl, or halogen; and $R^{13''}$ is hydrogen, alkyl, aryl, or halogen, preferably $R^{12''}$ and $R^{13''}$ are the same.

In any embodiment described herein, $R^6$, $R^7$, $R^8$, $R^9$, $R^{15}$, and $R^{16}$ may be, independently, selected from the group consisting of hydrogen, hydrocarbyls, substituted hydrocarbyls, alkoxy, halogen, amino, and silyl.

In any embodiment described herein, $R^1$, $R^3$, $R^4$, $R^5$, and $R^{11}$ may each contain from 1 to 30 carbon atoms, preferably $R^1$, $R^3$, $R^4$, $R^5$, $R^6$, $R^7$, $R^8$, $R^9$, $R^{15}$, and $R^{16}$ each contain from 1 to than 30 carbon atoms.

In any embodiment described herein, E is carbon and $R^1$ and $R^{11}$ are independently selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyls groups with from one to ten carbons.

In a preferred embodiment, the pyridyldiamido transition metal complex is represented by the Formula (A) or (B) above, and M is a Group 4 metal preferably Zr or Hf, preferably Hf.

In a preferred embodiment, the pyridyldiamido transition metal complex is represented by the Formula (I) or (II) above, and M is a Group 4 metal preferably Zr or Hf, preferably Hf.

In a preferred embodiment, the pyridyldiamido transition metal complex is represented by the Formula (A), (B), (I) or (II) above, and in the $R^{10}$ group $R^{12}$ is H and $R^{13}$ is a group containing between 1 to 100 (preferably 6 to 40, preferably 6 to 30) carbons, M is a Group 4 metal (preferably Zr or Hf, preferably Hf), E is carbon, and in the $R^2$ group $R^{12}$ is the same as $R^{13}$ and is preferably hydrogen or methyl.

In a preferred embodiment, the pyridyldiamido transition metal complex is represented by the Formula (A), (B), (I) or (II) above, and both $R^{12}$ and $R^{13}$ in the $R^2$ group are a $C_1$ to $C_{100}$ alkyl group (preferably a $C_6$ to $C_{40}$ alkyl group, preferably $C_6$ to $C_{30}$ alkyl group, alternately a $C_1$ to $C_{12}$ alkyl group, alternately a $C_1$ to $C_6$ alkyl group, alternately methyl, ethyl, propyl, butyl, pentyl hexyl, octyl, nonyl, decyl, or an isomer thereof).

In a preferred embodiment, the pyridyldiamido transition metal complex is represented by the Formula (A), (B), (I) or (II) above, and in the $R^2$ group $R^{12}$ is H, $R^{13}$ is a group containing between 1 to 100 (preferably 6 to 40, preferably 6 to 30) carbons, M is a Group 4 metal (preferably Zr or Hf, preferably Hf), E is carbon, and in the $R^{10}$ group $R^{12}$ is the same as $R^{13}$ and is preferably hydrogen or methyl.

In a preferred embodiment, the complexes described herein are diastereoisomeric mixtures of said complexes, which when used with activators to oligomerize or polymerize alkenes may give polyolefin products with bi- or multimodal polydispersities (Mw/Mn).

Specifically the complexes described herein are preferably used in diastereoisomeric mixtures where the diastereoisomers are present in ratios of 1:6 to 6:1, preferably 1:3 to 3:1, preferably 1:2 to 2:1. In the event that more than two diastereoisomeric species are present, then only the two predominant species are considered for the above ratio. Preferably there are no more than two diastereoisomeric species and if more than two species exist in the mixture, then the other species should not be present at more than 10 mol % of the two major species (as determined by $^1$H NMR spectra signal intensity.)

In a second aspect of the invention there are provided various processes for synthesizing the complexes described herein.

Ligand Synthesis

The pyridyl diamine ligands described herein are generally prepared in multiple steps. One step involves the preparation of an amine-containing "linker" group where the linker is typically a boronic acid ester of an aryl methyl amine or substituted amine. This amine-containing linker may be prepared from an aryl-methyl boronic ester in two steps, the first of which involves the conversion of the methyl group to a halo-methyl group by free radical halogenation in unreactive solvents (e.g., $CCl_4$, benzene). The second step then involves reaction of this halo-methyl group containing species with an amine or protected amine or deprotonated protected amine to yield an amine-containing linker. This amine-containing linker is then coupled with a suitable pyridine containing species, such as 6-bromo-2-pyridinecarboxaldehyde. This coupling step typically uses a metal catalyst (e.g., $Pd(PPh_3)_4$) in less than 5 mol % loading. Following this coupling step, the new derivative, which can be described as amine-linker-pyridine-aldehyde, is then reacted with a second amine to produce the imine derivative amine-linker-pyridine-imine in a condensation reaction. This can then be reduced to the pyridyl diamine ligand by reaction with a suitable aryl anion, alkyl anion, or hydride source. This reaction is generally performed in etherial solvents at temperatures between $-100°$ C. and $50°$ C. when aryllithium or alkyllithium reagents are employed. This reaction is generally performed in methanol at reflux when sodium cyanoborohydride is employed.

The preparation of pyridyl diamide metal complexes from pyridyl diamines may be accomplished using typical protonolysis and methylation reactions. In the protonolysis reaction the pyridyl diamine is reacted with a suitable metal reactant to produce a pyridyldiamide metal complex. A suitable metal reactant will feature a basic leaving group that will accept a proton from the pyridiyl diamine and then generally depart and be removed from the product. Suitable metal reactants include, but are not limited to, $HfBn_4$ ($Bn=CH_2Ph$), $ZrBn_4$, $TiBn_4$, $ZrBn_2Cl_2(OEt_2)$, $HfBn_2Cl_2(OEt_2)_2$, $Zr(NMe_2)_2Cl_2(dimethoxyethane)$, $Hf(NMe_2)_2Cl_2$ (dimethoxyethane), $Hf(NMe_2)_4$, and $Hf(NEt_2)_4$. Pyridyldiamide (PDA) metal complexes that contain metal-chloride groups, such as the PDA dichloride complex in Scheme 1 below, can be alkylated by reaction with an appropriate organometallic reagent. Suitable reagents include organolithium and organomagnesium, and Grignard reagents. The alkylations are generally performed in etherial or hydrocarbon solvents or solvent mixtures at temperatures typically ranging from $-100°$ C. to $50°$ C.

Scheme 1

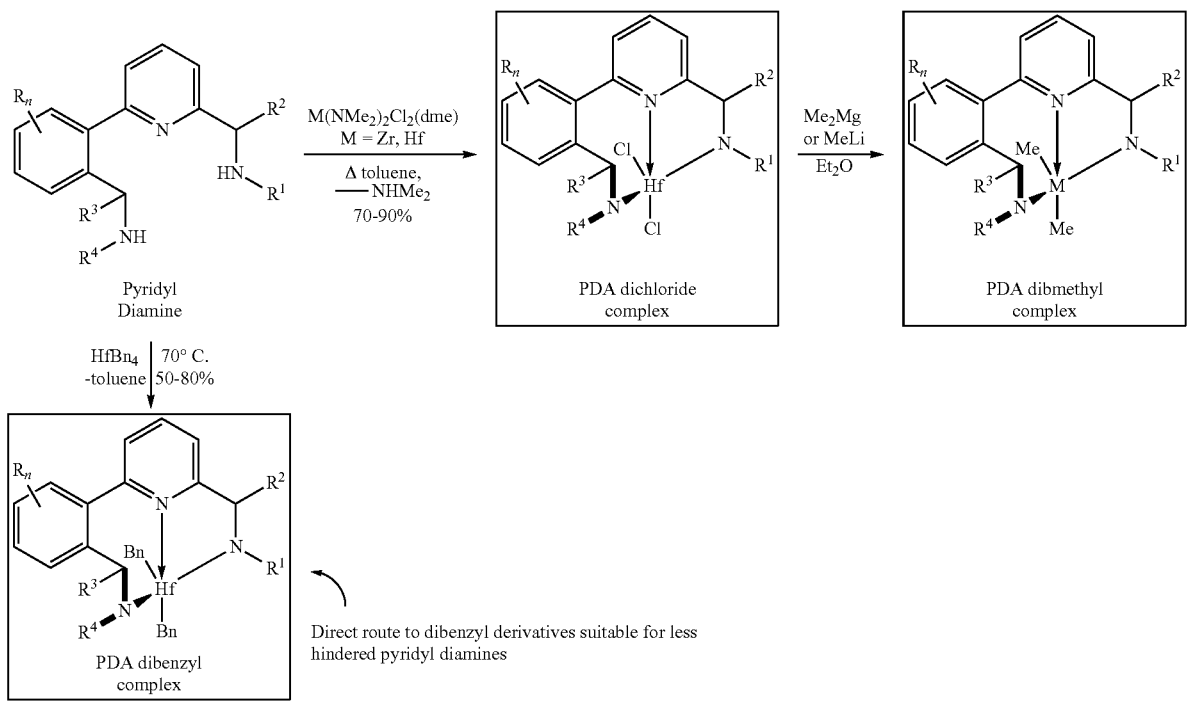

Direct route to dibenzyl derivatives suitable for less hindered pyridyl diamines where in Scheme 1, R, $R^1$, $R^2$, $R^3$, $R^4$ are independently selected from the group consisting of H, hydrocarbyls (such as alkyls, aryls), substituted hydrocarbyls (such as heteroaryls), and silyl groups, and $R_n$ indicates hydrogen, hydrocarbyls, or substituted hydrocarbyls, which may be joined to form polycyclic aromatic rings and n is 1, 2, 3, or 4.

Another route to pyridyl diamide and other complexes of interest as catalysts involves the insertion of an unsaturated molecule into a covalent metal-carbon bond where the covalently bonded group is part of a multidentate ligand structure, such as that described by Boussie et al. in U.S. Pat. No. 6,750,345. The unsaturated molecule will generally have a carbon-X double or triple bond where X is a group 14 or group 15 or group 16 element. Examples of unsaturated molecules include alkenes, alkynes, imines, nitriles, ketones, aldehydes, amides, formamides, carbon dioxide, isocyanates, thioisocyanates, and carbodiimides. Examples showing the insertion reactions involving benzophenone and N,N-dimethylformamide are below.

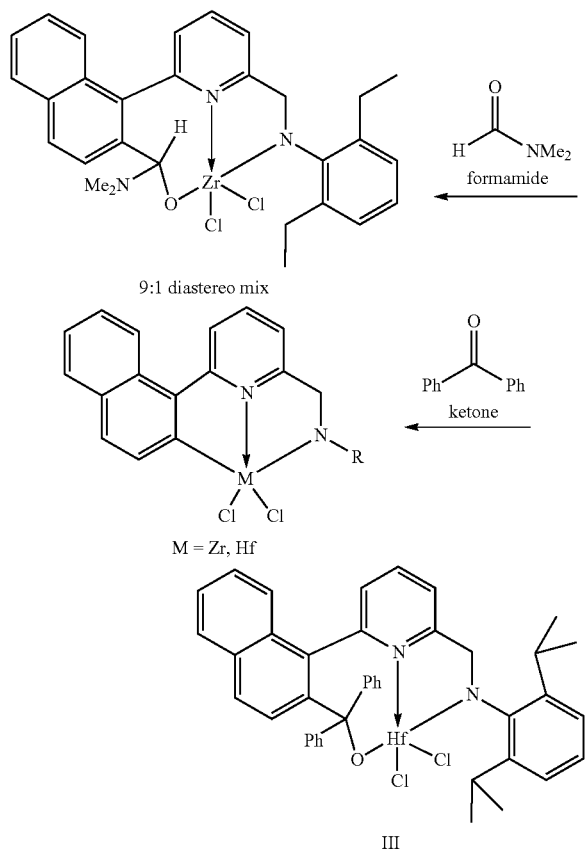

Pyridyl diamide complexes may have fluxional structures in solution.

This fluxional process may be used to develop "fluxional catalysts", which may be used to produce polymeric products containing blocky structures. A polyolefin molecule with a blocky structure has a non-homogeneous compositional and/or stereochemical distribution of monomers along the polymeric chain.

Without wishing to be bound by theory, the inventors suggest that changing the substituents at the $R^{10}$ position and/or changing the L and/or L' groups may allow for tailoring of the fluxional nature of the pyridylamido complex. The inventors' studies indicate that the above described fluxionality is fastest for pyridyl diamide (PDA) complexes of the general formula $(PDA)MX_2$, where X is alkyl, the PDA ligand lacks substitution at the $R^{10}$ position (based on Formula (B) described herein), and Z is a benzenyl (i.e., $C_6H_4$) group. Substitution of the PDA ligand at the $R^{10}$ position appears to hinder the fluxionality of the complex. Changing the X groups from alkyl to halide appears to further hinder the fluxionality. Changing Z to naphthalenyl (i.e., $C_{10}F_6$) appears to stop the fluxionality.

Based on these observations, the inventors suggest that one method for controlling the fluxionalty in these systems may be to use a sub-stoichiometric amount of a non-coordinating activator to form a mixture of activated and unactivated species. Of the two, the unactivated species would be expected to undergo relatively fast fluxionality, thereby favoring the non-homogenous incorporation of comonomers and the production of blocky polyolefins. The production of blocky polyolefins may be further improved when this system is employed in the presence of Group 12 or 13 organometallics (e.g., $ZnEt_2$, $AlEt_3$) that may facilitate polymeryl chain transfer.

Activators

After the complexes have been synthesized, catalyst systems may be formed by combining them with activators in any manner known from the literature including by supporting them for use in slurry or gas phase polymerization. The catalyst systems may also be added to or generated in solution polymerization or bulk polymerization (in the monomer). The catalyst system typically comprise a complex as described above and an activator such as alumoxane or a non-coordinating anion. Activation may be performed using alumoxane solution including methyl alumoxane, referred to as MAO, as well as modified MAO, referred to herein as MMAO, containing some higher alkyl groups to improve the solubility. Particularly useful MAO can be purchased from Albemarle in a 10 wt % solution in toluene. The catalyst system employed in the present invention preferably uses an activator selected from alumoxanes, such as methyl alumoxane, modified methyl alumoxane, ethyl alumoxane, iso-butyl alumoxane, and the like.

When an alumoxane or modified alumoxane is used, the complex-to-activator molar ratio is from about 1:3000 to 10:1; alternatively, 1:2000 to 10:1; alternatively 1:1000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1. When the activator is an alumoxane (modified or unmodified), some embodiments select the maximum amount of activator at a 5000-fold molar excess over the catalyst precursor (per metal catalytic site). The preferred minimum activator-to-complex ratio is 1:1 molar ratio.

Activation may also be performed using non-coordinating anions, referred to as NCA's, of the type described in EP 277 003 A1 and EP 277 004 A1. NCA may be added in the form of an ion pair using, for example, $[DMAH]^+$ $[NCA]^-$ in which the N,N-dimethylanilinium (DMAH) cation reacts with a basic leaving group on the transition metal complex to form a transition metal complex cation and $[NCA]^-$. The cation in the precursor may, alternatively, be trityl. Alternatively, the transition metal complex may be reacted with a neutral NCA precursor, such as $B(C_6F_5)_3$, which abstracts an anionic group from the complex to form an activated species. Useful activators include N,N-dimethylanilinium tetrakis(pentafluorophenyl)borate (i.e., $[PhNMe_2H]B(C_6F_5)_4$) and N,N-dimethylanilinium tetrakis(heptafluoronaphthyl)borate, where Ph is phenyl, and Me is methyl.

Additionally, preferred activators useful herein include those described in U.S. Pat. No. 7,247,687 at column 169, line 50 to column 174, line 43, particularly column 172, line 24 to column 173, line 53.

When an NCA (such as an ionic or neutral stoichiometric activator) is used, the complex-to-activator molar ratio is typically from 1:10 to 1:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1:1; 1:5 to 10:1; 1:5 to 2:1; 1:5 to 3:1; 1:5 to 5:1; 1:1 to 1:1.2.

Alternately, a co-activator may also be used in the catalyst system herein. The complex-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Supports

In some embodiments, the complexes described herein may be supported (with or without an activator) by any method effective to support other coordination catalyst systems, effective meaning that the catalyst so prepared can be used for oligomerizing or polymerizing olefin in a heterogeneous process. The catalyst precursor, activator, co-activator if needed, suitable solvent, and support may be added in any order or simultaneously. Typically, the complex and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The complex may also be supported absent the activator; in that case, the activator (and co-activator if needed) is added to a polymerization process's liquid phase. Additionally, two or more different complexes may be placed on the same support. Likewise, two or more activators or an activator and co-activator may be placed on the same support.

Suitable solid particle supports are typically comprised of polymeric or refractory oxide materials, each being preferably porous. Preferably any support material that has an average particle size greater than 10 μm is suitable for use in this invention. Various embodiments select a porous support material, such as for example, talc, inorganic oxides, inorganic chlorides, for example magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component, however, an additional activator may also be used.

The support material may be pretreated by any number of methods. For example, inorganic oxides may be calcined, chemically treated with dehydroxylating agents such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Useful supports typically have a surface area of from 10-700 $m^2/g$, a pore volume of 0.1-4.0 cc/g and an average particle size of 10-500 μm. Some embodiments select a surface area of 50-500 $m^2/g$, a pore volume of 0.5-3.5 cc/g, or an average particle size of 20-200 μm. Other embodiments select a surface area of 100-400 $m^2/g$, a pore volume of 0.8-3.0 cc/g, and an average particle size of 30-100 μm. Useful supports typically have a pore size of 10-1000 Angstroms, alternatively 50-500 Angstroms, or 75-350 Angstroms.

The catalyst complexes described herein are generally deposited on the support at a loading level of 10-100 micromoles of complex per gram of solid support; alternately 20-80 micromoles of complex per gram of solid support; or 40-60 micromoles of complex per gram of support. But greater or lesser values may be used provided that the total amount of solid complex does not exceed the support's pore volume.

Polymerization

Inventive catalyst complexes are useful in polymerizing unsaturated monomers conventionally known to undergo metallocene-catalyzed polymerization such as solution, slurry, gas-phase, and high-pressure polymerization. Typically one or more of the complexes described herein, one or more activators, and one or more monomers are contacted to produce polymer. In certain embodiments, the complexes may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The complexes, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the complex is activated in the reactor in the presence of olefin.

In a particularly preferred embodiment, the polymerization process is a continuous process.

Polymerization processes used herein typically comprise contacting one or more alkene monomers with the complexes (and, optionally, activator) described herein. For purpose of this invention alkenes are defined to include multi-alkenes (such as dialkenes) and alkenes having just one double bond. Polymerization may be homogeneous (solution or bulk polymerization) or heterogeneous (slurry-in a liquid diluent, or gas phase-in a gaseous diluent). In the case of heterogeneous slurry or gas phase polymerization, the complex and activator may be supported. Silica is useful as a support herein. Chain transfer agents (such as hydrogen, or diethyl zinc) may be used in the practice of this invention.

The present polymerization processes may be conducted under conditions preferably including a temperature of about 30° C. to about 200° C., preferably from 60° C. to 195° C., preferably from 75° C. to 190° C. The process may be conducted at a pressure of from 0.05 MPa to 1500 MPa. In a preferred embodiment, the pressure is between 1.7 MPa and 30 MPa, or in another embodiment, especially under supercritical conditions, the pressure is between 15 MPa and 1500 MPa.

The inventors have noted that polymerization temperature appears to affect the bimodal or multimodal nature of the polymer produced. Therefore, one of ordinary skill in the art will naturally vary the temperature systematically to determine the most efficacious temperature for any individual catalyst. This can be done, for example, by performing a series of polymerizations from 30° C. to 200° C., e.g., begin with the first polymerization run at 30° C. and then increase the polymerization temperature by 10° C. for each successive run. Preferably the polymerization series is conducted from 40 to 120° C.

Monomers

Monomers useful herein include olefins having from 2 to 20 carbon atoms, alternately 2 to 12 carbon atoms (preferably ethylene, propylene, butylene, pentene, hexene, heptene, octene, nonene, decene, and dodecene) and optionally also polyenes (such as dienes). Particularly preferred monomers include ethylene, and mixtures of $C_2$ to $C_{10}$ alpha olefins, such as ethylene-propylene, ethylene-hexene, ethylene-octene, propylene-hexene, and the like.

The complexes described herein are also particularly effective for the polymerization of ethylene, either alone or in combination with at least one other olefinically unsaturated monomer, such as a $C_3$ to $C_{20}$ α-olefin, and particularly a $C_3$ to $C_{12}$ α-olefin. Likewise, the present complexes are also particularly effective for the polymerization of propylene, either alone or in combination with at least one other olefinically unsaturated monomer, such as ethylene or a $C_4$ to $C_{20}$ α-olefin, and particularly a $C_4$ to $C_{20}$ α-olefin. Examples of preferred α-olefins include ethylene, propylene, butene-1, pentene-1, hexene-1, heptene-1, octene-1, nonene-1, decene-1, dodecene-1,4-methylpentene-1,3-methylpentene-1,3,5,5-trimethylhexene-1, and 5-ethylnonene-1.

In some embodiments, the monomer mixture may also comprise one or more dienes at up to 10 wt %, such as from 0.00001 to 1.0 wt %, for example from 0.002 to 0.5 wt %, such as from 0.003 to 0.2 wt %, based upon the monomer mixture. Non-limiting examples of useful dienes include, cyclopentadiene, norbornadiene, dicyclopentadiene, 5-ethylidene-2-norbornene, 5-vinyl-2-norbornene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1 and 9-methyl-1,9-decadiene.

Where olefins are used that give rise to short chain branching, such as propylene, the catalyst systems may, under appropriate conditions, generate stereoregular polymers or polymers having stereoregular sequences in the polymer chains.

Scavengers

In some embodiments, when using the complexes described herein, particularly when they are immobilized on a support, the catalyst system will additionally comprise one or more scavenging compounds. Here, the term scavenging compound means a compound that removes polar impurities from the reaction environment. These impurities adversely affect catalyst activity and stability. Typically, the scavenging compound will be an organometallic compound such as the Group-13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or $C_6$-$C_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, $[Me_2HNPh]^+[B(pfp)_4]^-$ or $B(pfp)_3$ (perfluorophenyl=pfp=$C_6F_5$).

In a preferred embodiment, two or more complexes are combined with diethyl zinc in the same reactor with monomer. Alternately, one or more complexes is combined with another catalyst (such as a metallocene) and diethyl zinc in the same reactor with monomer.

Polymer Products

While the molecular weight of the polymers produced herein is influenced by reactor conditions including temperature, monomer concentration and pressure, the presence of chain terminating agents and the like, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC. Preferred polymers produced here may be homopolymers or copolymers. In a preferred embodiment, the comonomer(s) are present at up to 50 mol %, preferably from 0.01 to 40 mol %, preferably 1 to 30 mol %, preferably from 5 to 20 mol %.

Figure 13:
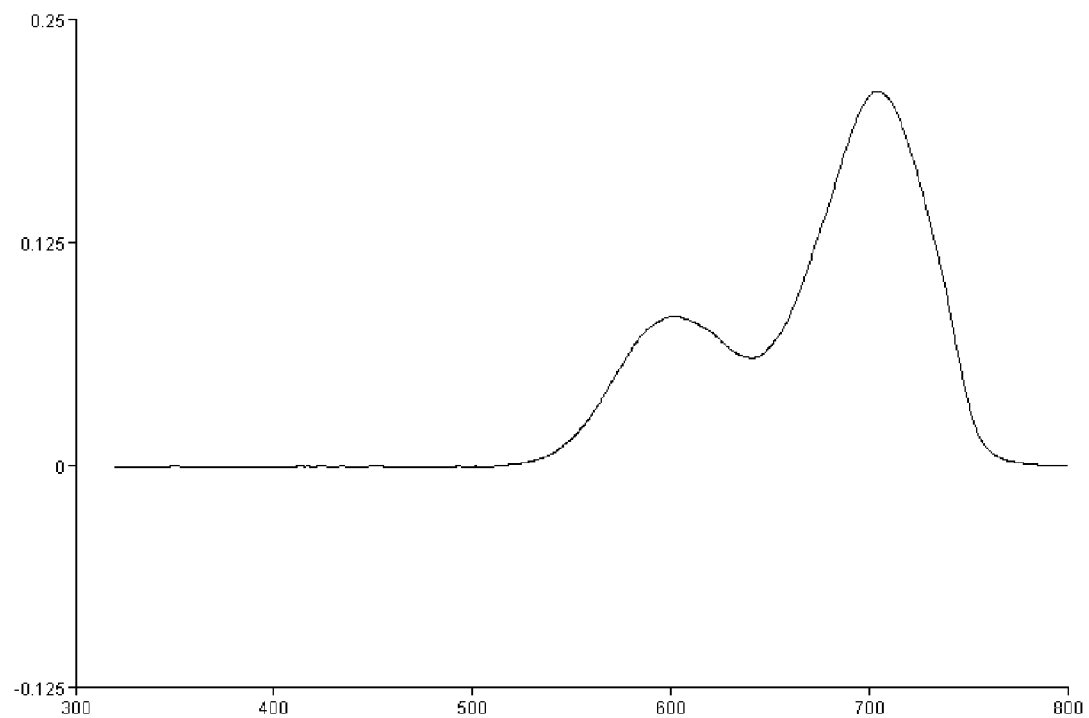
FIG. 13 is a GPC trace for run 8 of Table 2.
Figure 14:
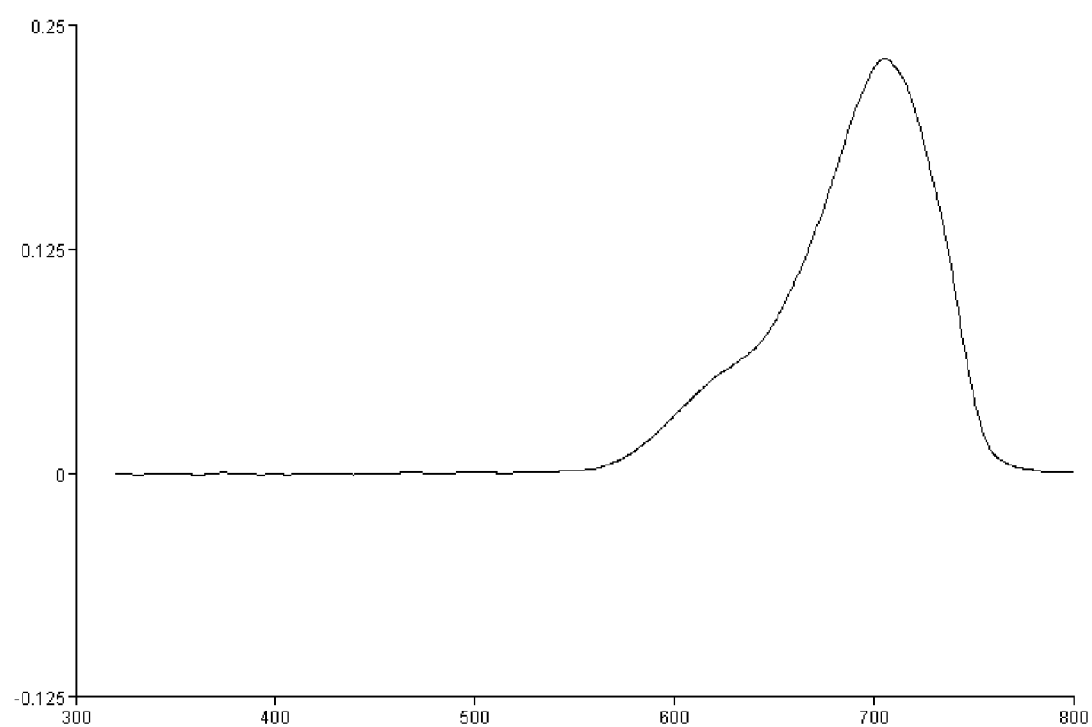
FIG. 14 is a GPC trace for run 9 of Table 2.

In some embodiments herein, a multimodal polyolefin composition is produced, comprising a first polyolefin component and at least another polyolefin component, different from the first polyolefin component by molecular weight, preferably such that the GPC trace has more than one peak or inflection point. The nature of the multimodal polyolefin composition produced by inventive processes of the present application is illustrated by FIGS. 13 and 14.

Measurements of weight average molecular weight (Mw), number average molecular weight (Mn), and z average molecular weight (Mz) are determined by Gel Permeation Chromatography (GPC) as described in Macromolecules, 2001, Vol. 34, No. 19, pg. 6812, which is fully incorporated herein by reference, including that, a High Temperature Size Exclusion Chromatograph (SEC, Waters Alliance 2000), equipped with a differential refractive index detector (DRI) equipped with three Polymer Laboratories PLgel 10 mm Mixed-B columns is used. The instrument is operated with a flow rate of 1.0 cm3/min, and an injection volume of 300 μL. The various transfer lines, columns and differential refractometer (the DRI detector) are housed in an oven maintained at 145 C. Polymer solutions are prepared by heating 0.75 to 1.5 mg/mL of polymer in filtered 1,2,4-Trichlorobenzene (TCB) containing ~1000 ppm of butylated hydroxy toluene (BHT) at 160° C. for 2 hours with continuous agitation. A sample of the polymer containing solution is injected into to the GPC and eluted using filtered 1,2,4-trichlorobenzene (TCB) containing ~1000 ppm of BHT. The separation efficiency of the column set is calibrated using a series of narrow MWD polystyrene standards reflecting the expected Mw range of the sample being analyzed and the exclusion limits of the column set. Seventeen individual polystyrene standards, obtained from Polymer Laboratories (Amherst, Mass.) and ranging from Peak Molecular Weight (Mp) ~580 to 10,000,000, were used to generate the calibration curve. The flow rate is calibrated for each run to give a common peak position for a flow rate marker (taken to be the positive inject peak) before determining the retention volume for each polystyrene standard. The flow marker peak position is used to correct the flow rate when analyzing samples. A calibration curve (log(Mp) vs. retention volume) is generated by recording the retention volume at the peak in the DRI signal for each PS standard, and fitting this data set to a 2nd-order polynomial. The equivalent polyethylene molecular weights are determined by using the Mark-Houwink coefficients shown in Table B.

TABLE B

Mark-Houwink coefficients

| Material | K (dL/g) | α |
|---|---|---|
| PS | $1.75 \times 10^{-4}$ | 0.67 |
| PE | $5.79 \times 10^{-4}$ | 0.695 |

In a preferred embodiment, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC and have a multi-modal, preferably bimodal, Mw/Mn.

End Uses

Articles made using polymers produced herein may include, for example, molded articles (such as containers and bottles, e.g., household containers, industrial chemical containers, personal care bottles, medical containers, fuel tanks, and storageware, toys, sheets, pipes, tubing) films, non-wovens, and the like. It should be appreciated that the list of applications above is merely exemplary, and is not intended to be limiting.

In another embodiment, this invention relates to:

1. In a first aspect of the invention there is provided a pyridyldiamido transition metal complex (optionally for use in alkene polymerization) represented by the formula (A) or (B):

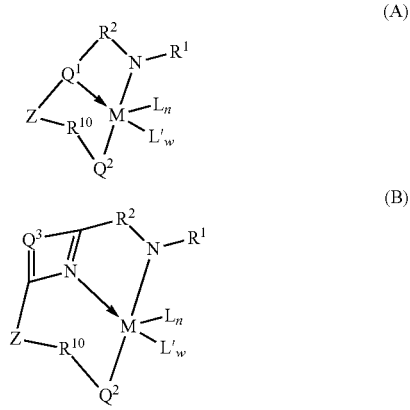

wherein:

M is a Group 3, 4, 5, 6, 7, 8, 9, 10, 11, or 12 metal;

$Q^1$ is a group that links $R^2$ and Z by a three atom bridge with the central of the three atoms being a group 15 or 16 element that preferably forms a dative bond to M preferably represented by the formula: $-G^1-G^2-G^3-$ where $G^2$ is a group 15 or 16 atom (preferably N, S, P or O, preferably N or P, preferably N), $G^1$ and $G^3$ are each a group 14, 15, or 16 atom, preferably C, Si, N, S, P, or O, where $G^1$, $G^2$ and $G^3$, or $G^1$ and $G^2$, or $G^1$ and $G^3$, or $G^2$ and $G^3$ may form a singular or multi ring system, and if any of $G^1$ and/or $G^3$ is a group 14 atom (such as C or Si) then $R^{30}$ and $R^{31}$ are bound to such G atom(s), and if any of $G^1$, $G^2$, and/or $G^3$ is a group 15 atom (such as N or P) then $R^{30}$ is bound to such G atom(s), where each $R^{30}$ and $R^{31}$ is, independently, hydrogen or a $C_1$ to $C_{100}$ hydrocarbyl group (alternately a $C_1$ to $C_{40}$, alternately a $C_1$ to $C_{20}$ hydrocarbyl group);

$Q^2$ is a group that forms an anionic bond with M, including but not limited to a group 16 element (such as O or S) or $NR^{17}$ or $PR^{17}$, where $R^{17}$ is selected from hydrogen, hydrocarbyls, substituted hydrocarbyls, alkoxy, aryloxy, halogen, amino, and silyl;

$Q^3$ is -(TT)- or -(TTT)- (where each T is carbon or a heteroatom, preferably C, O, S, or N, and said carbon or heteroatom may be unsubstituted (e.g., hydrogen is bound to the carbon or heteroatom or substituted with one or more $R^{30}$ groups) that together with the "—C-$Q^3$=C—" fragment, forms a 5- or 6-membered cyclic group or a polycyclic group including the 5- or 6-membered cyclic group;

$R^1$ is selected from the group consisting of hydrocarbyls, and substituted hydrocarbyls, or silyl groups;

$R^2$ and $R^{10}$ are each, independently, -$E(R^{12})(R^{13})$— with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

Z is —$(R^{14})_pC$—$C(R^{15})_q$—, where $R^{14}$ and $R^{15}$ are independently selected from the group consisting of hydrogen, hydrocarbyls (such as alkyls), and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings;

p is 0, 1, or 2;

q is 0, 1, or 2;

provided that one of $R^2$ and $R^{10}$ is asymmetrically substituted and the other is symmetrically substituted;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3, or 4; and wherein n+w is no greater than 4;

provided that one of $R^2$ and $R^{10}$ is asymmetrically substituted and the other is symmetrically substituted.

2. The complex of paragraph 1, wherein $Q^1$ is a substituted or unsubstituted pyridine group linked to Z and $R^2$ through the carbons in the 2 and 6 position (of the pyridine ring, with the nitrogen being the 1 position).

3. The complex of paragraph 1 or 2, wherein $G^1$ and $G^3$ are each independently selected from C, N, O, and S, preferably $G^1$ and $G^3$ with their respective R groups are methyl, ethyl, propyl, butyl, pentyl, hexyl, octyl, and the like, preferably $G^1$ and $G^3$ with their respective R groups are formed into a ring structure, preferably pyridine.

4. The complex of paragraph 1, 2, or 3, wherein $Q^2$ is $NR^{17}$, where $R^{17}$ is preferably a phenyl group or a substituted phenyl group, wherein when $R^{17}$ is substituted, $R^{17}$ is substituted with between one to five substituents that include F, Cl, Br, I, $CF_3$, $NO_2$, alkoxy, dialkylamino, aryl, and alkyl groups having 1 to 10 carbons, such as methyl, ethyl, propyl, butyl, pentyl, hexyl, heptyl, octyl, nonyl, decyl, and isomers thereof.

5. The complex of paragraph 1, 2, 3, or 4, wherein $Q^3$ is a three carbon linker (CH—CH—CH) that forms a pyridine ring or $Q^3$ is two atom linker containing one carbon and one group 15 or 16 element such that the linker forms a five-membered heterocycle, such as an imidazole or substituted imidazole.

6. A pyridyldiamido transition metal complex (optionally for use in alkene polymerization) represented by the formula (I) or (II):

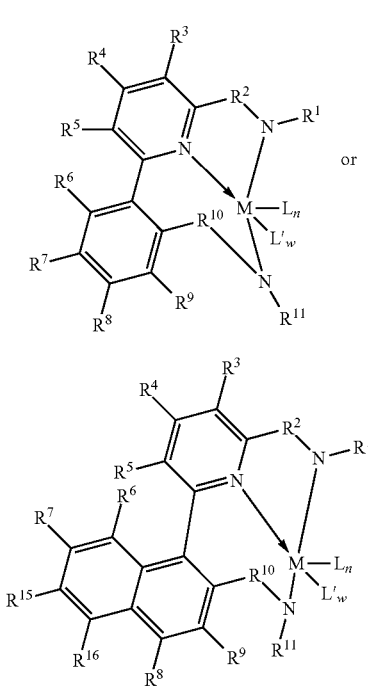

wherein:

M is a Group 3, 4, 5, 6, 7, 8, 9, 10, 11, or 12 metal;

$R^1$ and $R^{11}$ are independently selected from the group consisting of hydrocarbyls (such as alkyls and aryls), substituted hydrocarbyls (such as heteroaryls), and silyl groups;

$R^{10}$ and $R^2$ is each, independently, $-E(R^{12})(R^{13})-$ with E being carbon, silicon, or germanium, and each $R^{12}$ and $R^{13}$ being independently selected from the group consisting of hydrogen, hydrocarbyls (such as alkyls, aryls), alkoxy, silyl, amino, aryloxy, substituted hydrocarbyls (such as heteroaryl), halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

$R^3$, $R^4$, and $R^5$ are independently selected from the group consisting of hydrogen, hydrocarbyls (such as alkyls and aryls), substituted hydrocarbyls, alkoxy, aryloxy, halogen, amino, and silyl, and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^6$, $R^7$, $R^8$, $R^9$, $R^{15}$, and $R^{16}$ are independently selected from the group consisting of hydrogen, hydrocarbyls, substituted hydrocarbyls, alkoxy, halogen, amino, and silyl, and wherein adjacent R groups ($R^6$ & $R^7$, and/or $R^7$ & $R^{15}$, and/or $R^{16}$ & $R^{15}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3, or 4; and wherein n+w is no greater than 4;

provided that one of $R^2$ and $R^{10}$ is asymmetrically substituted and the other is symmetrically substituted.

7. Complex according to any of paragraphs 1 to 6 in which M is Ti, Zr, or Hf.

8. Complex according to any of paragraphs 1 to 7 in which $R^2$ is $CH_2$.

9. Complex according to any of paragraphs 1 to 8 in which $R^1$ and $R^3$ to $R^9$ and/or $R^{11}$ to $R^{15}$ above contain 1 to 30 carbon atoms, especially from 2 to 20 carbon atoms.

10. Complex according to any of paragraphs 1 to 9 in which E is carbon and $R^1$ and $R^{11}$ are independently selected from phenyl groups that are variously substituted with between zero to five substituents that include F, Cl, Br, I, $CF_3$, $NO_2$, alkoxy, dialkylamino, hydrocarbyl (such as alkyl and aryl), and substituted hydrocarbyls (such as heteroaryl), groups with from one to ten carbons.

11. Complex according to any of paragraphs 1 to 10 in which L is or are selected from halide, alkyl, aryl, alkoxy, amido, hydrido, phenoxy, hydroxy, silyl, allyl, alkenyl, and alkynyl; and/or L' is or are selected from ethers, thio-ethers, amines, nitriles, imines, pyridines, and phosphines.

12. The complex of any of paragraphs 1 to 11, wherein $R^2$ is represented by the formula:

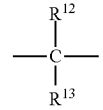

where $R^{12}$ is hydrogen, alkyl, aryl, or halogen; and $R^{13}$ is hydrogen, alkyl, aryl, or halogen.

13. The complex of any of paragraphs 1 to 12, wherein $R^6$, $R^7$, $R^8$, $R^9$, $R^{15}$, and $R^{16}$, are independently selected from the group consisting of hydrogen, hydrocarbyls, substituted hydrocarbyls, alkoxy, halogen, amino, and silyl.

14. The complex of any of paragraphs 1 to 13, wherein $R^1$, $R^3$, $R^4$, $R^5$, $R^{11}$ each contain from 1 to 30 carbon atoms.

15. The complex of any of paragraphs 1 to 14, wherein E is carbon and $R^1$ and $R^{11}$ are independently selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyls groups with from one to ten carbons.

16. The complex of any of paragraphs 1 to 15, wherein for $R^{10}$, E is carbon, $R^{12}$ is phenyl and $R^{13}$ is H.

17. The complex of any of paragraphs 1 to 16, wherein the $R^2$ group(s) are selected from the group consisting of $CH_2$, $CMe_2$, $SiMe_2$, $SiEt_2$, $SiPr_2$, $SiBu_2$, $SiPh_2$, $Si(aryl)_2$, and $Si(alkyl)_2$, CH(aryl), CH(Ph), CH(alkyl), CH(2-isopropylphenyl), and or the $R^{10}$ group(s) are selected from the group consisting of $CH_2$, $CMe_2$, $SiMe_2$, $SiEt_2$, $SiPr_2$, $SiBu_2$, $SiPh_2$, $Si(aryl)_2$, and $Si(alkyl)_2$, CH(aryl), CH(Ph), CH(alkyl), CH(2-isopropylphenyl), where alkyl is a $C_1$ to $C_{40}$ alkyl group, aryl is a $C_5$ to $C_{40}$ aryl group, and Ph is phenyl.

18. The complex of any of paragraphs 1 to 17, wherein $R^2$ is one or more of $CH_2$ and $CMe_2$, and $R^{10}$ is one or more of CH(Ph), CH(aryl), and CH(alkyl), where alkyl is a $C_1$ to $C_{40}$ alkyl group, aryl is a $C_5$ to $C_{40}$ aryl group, and Ph is phenyl.

19. The complex of any of paragraphs 1 to 18, wherein $R^2$ and $R^{10}$ groups (expressed as $R^2$ & $R^{10}$) are: ($CH_2$ & CH(Ph)), ($CMe_2$ and CH(Ph)), ($CH_2$ and CH(aryl)), ($CH_2$ and CH(alkyl)), where alkyl is a $C_1$ to $C_{40}$ alkyl group, aryl is a $C_5$ to $C_{40}$ aryl group and Ph is phenyl.

20. A catalyst system comprising an activator and the complex of any of paragraphs 1 to 19.

21. The catalyst system of paragraph 20, wherein the activator is an alumoxane and/or a non-coordinating anion.

22. The catalyst system of paragraph 20 or 21, wherein the catalyst system is supported.

23. A polymerization process to produce a multimodal polyolefin comprising:
   a) contacting one or more olefin monomers with the catalyst system of paragraph 20, 21, or 22; and
   b) obtaining multimodal olefin polymer.

24. The process of paragraph 23, wherein the monomer comprises ethylene and/or propylene.

EXAMPLES $^1$H NMR spectroscopic data were acquired at 250, 400, or 500 MHz using solutions prepared by dissolving approximately 10 mg of a sample in either $C_6D_6$, $CD_2Cl_2$, $CDCl_3$, or $D_8$-toluene. The chemical shifts (δ) presented are relative to the residual protium in the deuterated solvent at 7.15, 5.32, 7.24, and 2.09 for $C_6D_6$, $CD_2Cl_2$, $CDCl_3$, and $D_8$-toluene, respectively. For purposes of the claims 500 Mz and $CD_2Cl_2$.

Synthesis of Pyridyl Amines 2,6-Diethyl-N-((6-(naphthalen-1-yl)pyridin-2-yl)methyl) aniline and 2,6-diisopropyl-N-((6-phenylpyridin-2-yl)methyl)aniline were prepared following the general synthetic methods described in U.S. Pat. No. 6,900,321 B2.

Synthesis of Pyridyl Diamines

Outlined in Schemes 1 and 2 are general synthetic routes that were used to prepare pyridyl diamines. In the Schemes pin is pinacolate (2,3 dimethyl butane 2,3 diolate), Me is methyl, Mes is mesityl, Boc is t-butylcarbonate, t-Bu and tBu are t-butyl, Ph is phenyl, 2-Tol is ortho-tolyl, Dipp is 2,6-diisopropylphenyl, and 2-iPrPh is 2-isopropylphenyl.

Scheme 1.

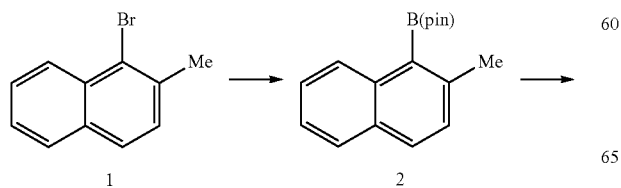

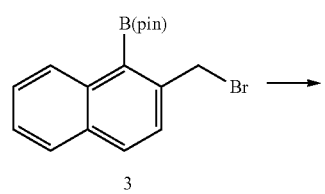

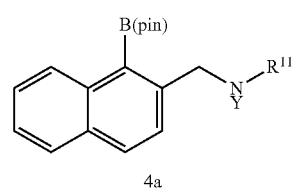

| | Y | $R^{11}$ |
|---|---|---|
| 4a | Boc | Ph |

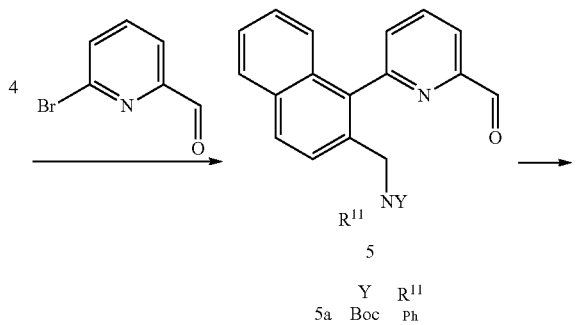

| | Y | $R^{11}$ |
|---|---|---|
| 5a | Boc | Ph |

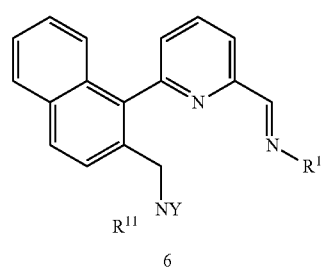

| | Y | $R^1$ | $R^{11}$ |
|---|---|---|---|
| 6a | Boc | Dipp | Ph |

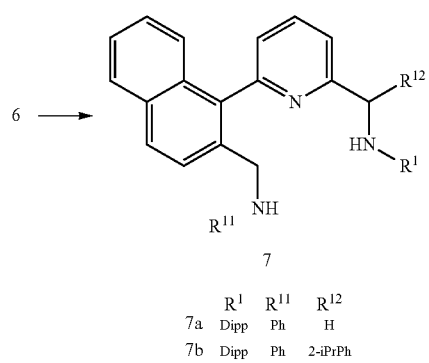

| | $R^1$ | $R^{11}$ | $R^{12}$ |
|---|---|---|---|
| 7a | Dipp | Ph | H |
| 7b | Dipp | Ph | 2-iPrPh |

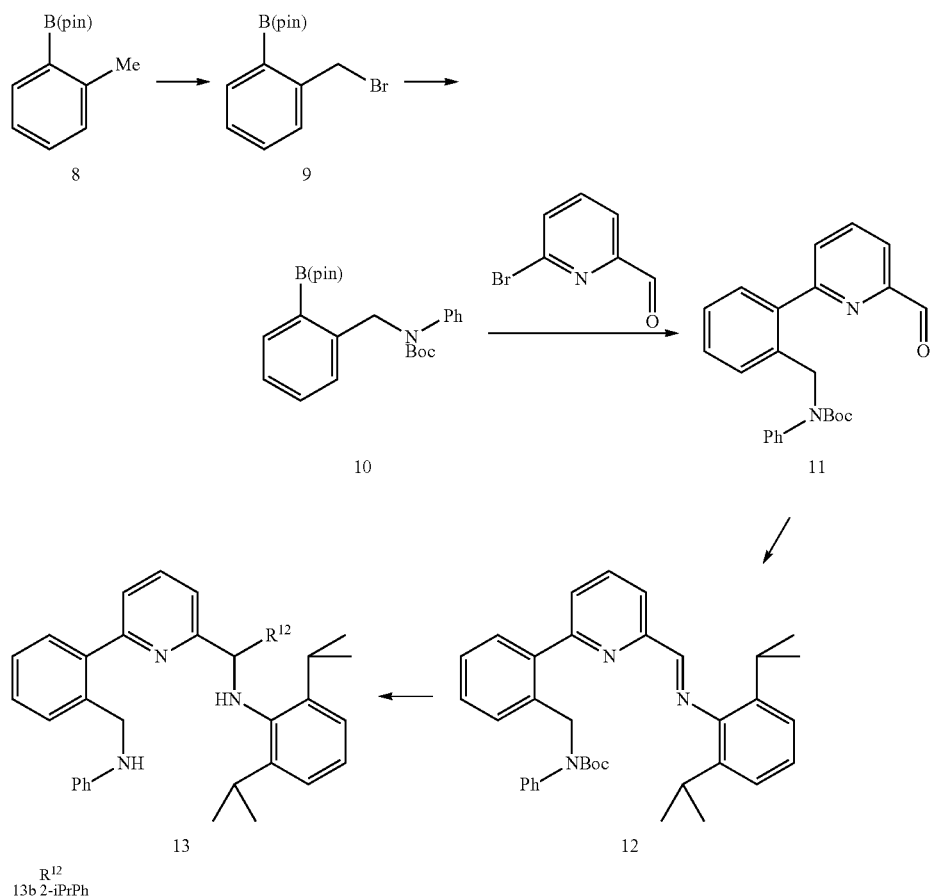

4,4,5,5-Tetramethyl-2-(2-methyl-1-naphthyl)-1,3,2-dioxaborolane (2)

1,2-Dibromoethane (~0.3 ml) was added to 6.10 g (250 mmol) magnesium turnings in 1000 cm³ of THF. This mixture was stirred for 10 min, and then 55.3 g (250 mmol) of 1-bromo-2-methylnaphthalene was added for 1 h by vigorous stirring at room temperature for 3.5 h. Further on, 46.5 g (250 mmol) of 2-isopropoxy-4,4,5,5-tetramethyl-1,3,2-dioxaborolane was added in one portion. The resulting mixture was stirred for 15 minutes and then was poured into 1000 cm³ of cold water. The product was extracted with 3×300 ml of ethyl acetate. The organic layer was separated, washed by water, brine, then dried over MgSO₄, and, finally, evaporated to dryness. The resulting white solid was washed by 2×75 ml of pentane and dried in vacuum. Yield 47.3 g (70%). ¹H NMR (CDCl₃): 8.12 (m, 1H, 8-H), 7.77 (m, 1H, 5-H), 7.75 (d, J=8.4 Hz, 1H, 4-H), 7.44 (m, 1H, 7-H), 7.38 (m, 1H, 6-H), 7.28 (d, J=8.4 Hz, 1H, 3-H), 2.63 (s, 3H, 2-Me), 1.48 (s, 12H, CMe₂CMe₂).

2-[2-(Bromomethyl)-1-naphthyl]-4,4,5,5-tetramethyl-1,3,2-dioxaborolane (3)

A mixture of 47.3 g (176 mmol) of 4,4,5,5-tetramethyl-2-(2-methyl-1-naphthyl)-1,3,2-dioxaborolane, 33.0 g (185 mmol) of NBS (N-Bromosuccinimide) and 0.17 g of benzoyl peroxide in 340 ml of CCl₄ was stirred at 75° C. for 14 h. Further on, the reaction mixture was cooled to room temperature, filtered through glass frit (G3), and the filtrate was evaporated to dryness. This procedure gave 62.2 g (99%) of beige solid. ¹H NMR (CDCl₃): 8.30 (m, 1H, 8-H), 7.84 (d, J=8.3 Hz, 1H, 4-H), 7.79 (m, 1H, 5-H), 7.43-7.52 (m, 3H, 3,6,7-H), 4.96 (s, 2H, CH₂Br), 1.51 (s, 12H, CMe₂CMe₂).

tert-Butyl phenyl{[1-(4,4,5,5-tetramethyl-1,3,2-dioxaborolan-2-yl)-2-naphthyl]-methyl}carbamate (4a)

To a suspension of 17.0 g (88.1 mmol) of tert-Butyl phenylcarbamate in 150 ml of hexanes 35.2 ml (88.1 mmol) of 2.5 M nBuLi in hexanes was slowly added at gentle reflux for ca. 15 min. This mixture was stirred for additional 30 minutes and then evaporated to dryness. The resulting white powder was added to a solution of 30.6 g (88.1 mmol) of 2-[2-(bromomethyl)-1-naphthyl]-4,4,5,5-tetramethyl-1,3,2-dioxaborolane in 300 ml of DMF. This mixture was stirred for 20 minutes at 75° C. and then poured into 1200 cm³ of cold water. The product was extracted with 3×200 ml of ethyl acetate. The combined organic extract was washed by 2×300 ml of water, dried over MgSO₄, and then evaporated to dryness. The crude product was purified by flash chromatography on silica gel 60 (40-63 um, eluent: hexanes-ethyl acetate=20:1, vol. then 10:1, vol.). Yield 28.0 g (69%) of yellowish oil. ¹H NMR (CDCl₃): 8.19 (m, 1H, 8-H in naphthyl), 7.85 (d, J=8.6 Hz, 1H, 4-H in naphthyl), 7.77 (m, 1H, 5-H in naphthyl), 7.60 (d, J=8.6 Hz, 1H, 3-H in naphthyl), 7.45 (m, 1H, 7-H in naphthyl), 7.40 (m, 1H, 6-H in naphthyl), 7.20 (m, 2H, 3,5-H in Ph), 7.13 (m, 2H, 2,6-H in Ph), 7.08 (m, 1H, 4-H in Ph), 5.21 (s, 2H, CH₂N), 1.42 (s, 9H, tBu), 1.38 (s, 12H, CMe₂CMe₂).

tert-Butyl {[1-(6-formylpyridin-2-yl)-2-naphthyl]methyl}phenylcarbamate (5a)

A solution of 24.3 g (84.8 mmol) of $Na_2CO_3(H_2O)_{10}$ in a mixture of 120 ml of methanol and 450 ml of water was added to a mixture of 6.30 g (33.9 mmol) of 6-bromopyridine-2-carbaldehyde, 15.6 g (33.9 mmol) of tert-butyl phenyl {[1-(4,4,5,5-tetramethyl-1,3,2-dioxaborolan-2-yl)-2-naphthyl]methyl}carbamate and 1.96 g (1.70 mmol) of $Pd(PPh_3)_4$ in 600 ml of toluene by vigorous stirring at room temperature. The resulting mixture was stirred at 80° C. for 12 h. Further on, this mixture was cooled to room temperature, the organic layer was separated, dried over $MgSO_4$, and then evaporated to dryness. The product was isolated by flash chromatography on silica gel 60 (40-63 um; eluent: hexanes-ethyl acetate=50:1 and then 10:1, vol.). Yield 9.50 g (64%). $^1$H NMR ($CDCl_3$): 10.03 (s, 1H, CHO), 7.94-7.98 (m, 2H, 3,5-H in Py), 7.88 (m, 1H, 8-H in naphthyl), 7.83 (m, 1H, 4-H in Py), 7.75 (d, J=8.6 Hz, 1H, 4-H in naphthyl), 7.45 (m, 1H, 7-H in naphthyl), 7.34 (m, 1H, 6-H in naphthyl), 7.11-7.18 (m, 4H, 5-H in naphthyl and 3,4,5-H in Ph), 7.03 (d, J=8.6 Hz, 1H, 3-H in naphthyl), 6.93 (m, 2H, 2,6-H in Ph), 5.06 (d, J=15.9 Hz, 1H, CHH'N), 4.52 (d, J=15.9 Hz, 1H, CHH'N), 1.40 (s, 9H, $^t$Bu).

2,6-Diisopropyl-N-((6-(2-((phenylamino)methyl)naphthalen-1-yl)pyridin-2-yl)methyl)aniline (7a)

Compound 5a (1.95 g, 4.43 mmol) and tetrahydrofuran (30 mL) were combined to form a solution. Then 2,6-diisopropylaniline (0.785 g, 4.43 mmol) and 4 angstrom molecular sieves (ca. 20 mL) were added followed by a catalytic amount of p-toluenesulfonic acid monohydrate (0.005 g, 0.03 mmol). The mixture became yellow immediately. After stirring overnight the mixture was filtered and evaporated to afford the imine 6a as an oil. This was then dissolved in methanol (30 mL) and $NaBH_3CN$ (0.45 g) was added followed by a few drops of 85% formic acid. The mixture was heated to reflux. Additional $NaBH_3CN$ (0.45 g) and a couple drops of the formic acid were added after 15 minutes. After another 15 minutes a third portion of $NaBH_3CN$ (0.45 g) and a couple drops of the formic acid were added. After a total of 2.5 hours at reflux the pale yellow mixture was poured into water (250 mL) and extracted with $Et_2O$ ($Et_2O$ is diethyl ether, 150 mL). The organics were dried with brine then evaporated to an oil with some water or methanol separating out. This was extracted with $Et_2O$ (20 mL), dried over magnesium sulfate, filtered, and evaporated to a residue containing the Boc-protected amine product. This was dissolved chloroform (40 mL) and trifluoroacetic acid (16 mL) was added. The mixture was heated to 55° C. for 1 hour, during which time gas evolved. The mixture was then poured into 3 M NaOH (125 mL) and stirred for several minutes. The organics were extracted into $Et_2O$ (200 mL) then separated, dried over sodium sulfate, and evaporated to a slightly colored oil. The crude product was purified by chromatography on basic alumina using 5:1 hexanes:$CH_2Cl_2$ with an increasing gradient of ethyl acetate (0.5% to 10%). The product was isolated as a thick, purple-tinted oil. $^1$H NMR (500 MHz, $CD_2Cl_2$): 7.93 (t, 2H), 7.85 (t, 1H), 7.69 (d, 1H), 7.37-7.52 (m, 5H), 7.00-7.11 (m, 5H), 6.63 (t, 1H), 6.57 (d, 2H), 4.06-4.37 (m, 6H), 3.33 (sept, 2H), 1.16 (d, 12H).

2,6-Diisopropyl-N-((2-isopropylphenyl)(6-(2-((phenylamino)methyl)naphthalen-1-yl)pyridin-2-yl)methyl)aniline (7b)

Compound 5a (2.28 g, 5.18 mmol), tetrahydrofuran (50 mL), and 4 angstrom molecular sieves (ca. 20 mL) were combined. Then 2,6-diisopropylaniline (0.918 g, 5.18 mmol) and a catalytic amount of p-toluenesulfonic acid monohydrate (0.005 g, 0.03 mmol) were added. The mixture was heated to 45° C. for 14 hours. Then the mixture was filtered and fresh molecular sieves (ca. 15 mL) were added followed by additional p-toluenesulfonic acid monohydrate (0.005 g, 0.03 mmol). After heating at 50° C. for 2 hours the mixture was filtered and evaporated to a residue of the imine 6a. Then $Et_2O$ (30 mL) was added, and the resulting solution was cooled to −80° C. An $Et_2O$ (5 mL) solution of 2-isopropylphenyllithium (0.653 g, 5.18 mmol) was added dropwise. The mixture was then allowed to slowly warm to ambient temperature over a couple of hours. Then the mixture was poured into water (100 mL) and the organics were separated, dried over brine then magnesium sulfate, filtered, and evaporated to a residue. The residue was dissolved in chloroform (25 mL), and trifluoroacetic acid (10 mL) was added. The mixture was heated to reflux for 40 minutes, during which time gas evolved. The mixture was cooled to ambient temperature and 3 M NaOH (60 mL) was added. After stirring for several minutes, the organics were separated, dried over brine then magnesium sulfate, filtered through diatomaceous earth, and evaporated to yield the crude product. This was purified by chromatography on basic alumina using 5:1 hexanes:$CH_2Cl_2$ with an increasing gradient of ethyl acetate (1% to 10%). The product was isolated as a foam-like solid.

tert-Butyl phenyl(2-(4,4,5,5-tetramethyl-1,3,2-dioxaborolan-2-yl)benzyl)carbamate (10)

Pentane (350 mL) was added to tert-butyl phenylcarbamate (20.81 g, 107.7 mmol) to form a suspension. BuLi (67.3 mL, 107.7 mmol) in hexanes was added dropwise over 1 hour. During the addition a clear solution formed briefly then a white precipitate formed. After the addition was complete the mixture was stirred for 1 hour then the solid was collected on a glass frit, washed with pentane (2×20 mL), and dried under reduced pressure to afford LiN(Boc)Ph (16.6 g, 77.4%). 2-Bromomethylphenyl boronic acid pinacol ester (compound 9) (4.66 g, 15.7 mmol) and N,N-dimethylformamide (DMF) (35 mL) were combined to form a clear colorless solution. Then solid LiN(Boc)Ph (3.13 g, 15.7 mmol) was added in small portions over three minutes. The mixture was stirred for 2 hours then the white suspension was poured into water (250 mL). $Et_2O$ (150 mL) was added and the organics were separated, dried with brine then magnesium sulfate. Filtration followed by evaporation afforded the product as a white solid. $^1$H NMR ($CDCl_3$, 250 MHz): 7.77 (d, 1H), 7.0-7.5 (m, 8H), 5.19 (s, 2H), 1.39 (s, 9H), 1.27 (s, 12H).

tert-Butyl 2-(6-formylpyridin-2-yl)benzyl(phenyl)carbamate (11)

A mixture of water (160 mL) and methanol (40 mL) was combined with sodium carbonate (3.80 g, 35.9 mmol), and the mixture was sparged with nitrogen for 30 min. In a separate flask were combined, under nitrogen, 6-bromo-2-pyridinecarboxaldehyde (2.67 g, 14.4 mmol), tert-butyl phenyl(2-(4,4,5,5-tetramethyl-1,3,2-dioxaborolan-2-yl)benzyl)carbamate (5.87 g, 14.4 mmol), tetrakis(triphenylphosphinio)palladium (0.829 g, 0.718 mmol), and toluene (150 mL). The water-methanol solution was added via cannula to the toluene solution, and the biphasic mixture was heated to 80° C. overnight. At this time $^1$H NMR spectroscopic analysis of an aliquot indicated that the reaction was complete. The clear yellow organic layer was separated, dried with brine, then over magnesium sulfate. The crude product was purified by chromatography on silica using 1:1 hexanes: dichloromethane elutant and increasing the strength by addition of up to 10% EtOAc. The product was isolated as a sticky oil (4.7 g, 840%). $^1$H NMR (CD$_2$Cl$_2$, 500 MHz): 10.0 (s, 1H), 7.83-7.92 (m, 2H), 7.56 (d, 1H), 7.50 (d, 1H), 7.44 (m, 1H), 7.36 (m, 2H), 7.17 (t, 2H), 7.01 (t, 1H), 7.0 (br d, 2H), 5.11 (s, 2H), 1.34 (s, 9H).

(E)-tert-Butyl 2-(6-((2,6-diisopropylphenylimino) methyl)pyridin-2-yl)benzyl-(phenyl)carbamate (12)

Tetrahydrofuran (50 mL) and 4 angstrom molecular sieves (ca. 15 mL) were added to tert-butyl 2-(6-formylpyridin-2-yl)benzyl(phenyl)carbamate (11) (03.63 g, 9.34 mmol). Then 2,6-diisopropylaniline (1.66 g, 9.34 mmol) was added followed by a catalytic amount of p-toluenesulfonic acid monohydrate (0.003 g, 0.015 mmol). The mixture was stirred overnight then filtered and evaporated to a thick yellow oil. After several days the oil began to crystallize. Methanol (40 mL) was added and the mixture was stirred to give a yellow crystalline solid. The mixture was cooled to 5° C. for a couple of hours then the solid was collected on a glass frit and dried under reduced pressure. Yield: 3.93 g, 76.8%. $^1$H NMR (CD$_2$Cl$_2$, 500 MHz): 8.26 (s, 1H), 8.19 (d, 1H), 7.87 (t, 1H), 7.54 (d, 1H), 7.32-7.42 (m, 4H), 7.02-7.20 (m, 8H), 5.11 (s, 2H), 2.99 (sept, 2H), 1.34 (s, 9H), 1.18 (d, 12H).

2,6-Diisopropyl-N-((2-isopropylphenyl)(6-(2-((phenylamino)methyl)phenyl)pyridin-2-yl)methyl)aniline (13b)

Et$_2$O (30 mL) and (E)-tert-butyl 2-(6-((2,6-diisopropylphenylimino)methyl)pyridin-2-yl)benzyl(phenyl)carbamate (12) (1.07 g (1.96 mmol) were combined to form a clear yellow solution. At −80° C. an Et$_2$O (3 mL) solution of 2-isopropylphenyllithium (0.247 g, 1.96 mmol) was added dropwise over a few minutes. The mixture was clear redorange. The mixture was allowed to slowly warm to ambient temperature. After stirring overnight water (20 mL) was added and the organic layer was separated. The organics were dried with brine, then over magnesium sulfate. Filtration and evaporation afforded a residue that was dissolved in CHCl$_3$ (10 mL). Trifluoroacetic acid (4 mL) was then added and the mixture was heated to reflux for 45 minutes during which time gas evolved. At ambient temperature 3 M NaOH (30 mL) was added and the biphasic mixture was stirred rapidly. Then Et$_2$O (40 mL) was added and the organics were separated, dried with brine, dried over magnesium sulfate, filtered, then evaporated to a thick oil. The product was dried thoroughly under reduced pressure (1.16 g, 104%). $^1$H NMR (CD$_2$Cl$_2$, 500 MHz): 7.66-7.73 (pseudo quartet, 2H), 7.32-7.50 (m, 5H), 7.15-7.26 (m, 4H), 6.96-7.05 (m, 5H), 6.58 (t, 1H), 6.37 (d, 2H), 5.49 (s, 1H), 4.22 (4H, m), 3.05 (sept, 1H), 2.87 (sept, 2H), 0.97 (d, 12H), 0.92 (d, 3H), 0.90 (d, 3H).

Synthesis of Pyridyl Diamide Metal Complexes

Described below in Table 1 are four pyridyl diamide metal complexes. Complexes F, I, and M were prepared by reaction of a pyridyl diamine with a suitable organometallic reagent containing two basic ligands that deprotonate the pyridyl diamine and form leaving groups, which are subsequently removed. Complexes R and S were prepared by the reaction of an imine with the appropriate pyridyl amide complex. This basic route was described in WO 2010/011435 A1. The $^1$H NMR spectra for complexes F, I, M, R, and S are shown in FIGS. 1-5. Complexes F, I, and M are not part of the invention and are for comparative purposes only.

TABLE 1

Pyridyl diamide complexes.

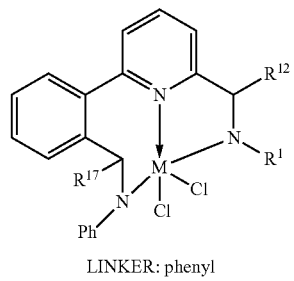

LINKER: phenyl

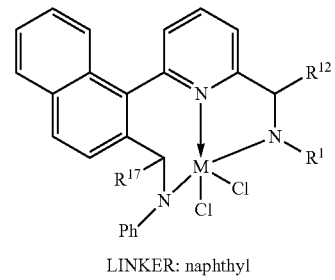

LINKER: naphthyl

| Complex | M | R$^1$ | R$^{12}$ | R$^{17}$ | LINKER |
|---|---|---|---|---|---|
| comparative | F | Hf | Dipp | H | H | Naphthyl |
| comparative | I | Zr | Dipp | 2-$^i$PrPh | H | Phenyl |
| comparative | M | Zr | Dipp | 2-$^i$PrPh | H | Naphthyl |
| inventive | R | Hf | Dipp | H | Ph | Phenyl |
| inventive | S | Zr | Dep | H | Ph | Naphthyl |

Complex F.

Benzene (4 mL) was added to 2,6-diisopropyl-N-((6-(2-((phenylamino)methyl)naphthalen-1-yl)pyridin-2-yl)methyl)aniline (7a) (0.150 g, 0.300 mmol) and HfBn$_2$Cl$_2$(OEt$_2$)$_{18}$ (0.170 g, 0.300 mmol). The mixture was heated to 50° C. for 1 hour. The volatiles were then evaporated and Et$_2$O (3 mL) was added to the residue. The resulting white solid was collected on a glass frit, washed with Et$_2$O (2 mL) and dried under reduced pressure. Yield 0.203 g, 90.6%.

Complex I.

Toluene (6 mL) was added to 2,6-diisopropyl-N-((2-isopropylphenyl)(6-(2-((phenylamino)methyl)phenyl)pyridin-2-yl)methyl)aniline (13b) (0.328 g, 0.578 mmol) and Zr(NMe$_2$)$_2$Cl$_2$(dme) (dme=1,2-dimethoxyethane) (0.197 g, 0.578 mmol). The mixture was heated to 100° C. for 2 hours. The volatiles were then evaporated and Et$_2$O (3 mL) was added to the residue. The resulting yellow solid was collected on a glass frit, washed with Et$_2$O (2 mL), and pentane (10 mL), and then dried under reduced pressure. Yield 0.281 g, 66.8%.

Complex M.

Benzene (5 mL) was added to 2,6-diisopropyl-N-((2-isopropylphenyl)(6-(2-((phenylamino)methyl)naphthalen-1-yl)pyridin-2-yl)methyl)aniline (7b) (0.251 g, 0.406 mmol) and Zr(NMe$_2$)$_2$Cl$_2$(dme) (dme=1,2-dimethoxyethane) (0.138 g, 0.406 mmol). The mixture was heated to 70° C. for 5 hours. Toluene (4 mL) was then added and the mixture was heated to 100° C. for 0.5 hours. The volatiles were then evaporated and Et$_2$O (3 mL) was added to the residue. The resulting yellow solid was collected on a glass frit, washed with Et$_2$O (2×2 mL), and then dried under reduced pressure. Yield 0.241 g, 76.3%.

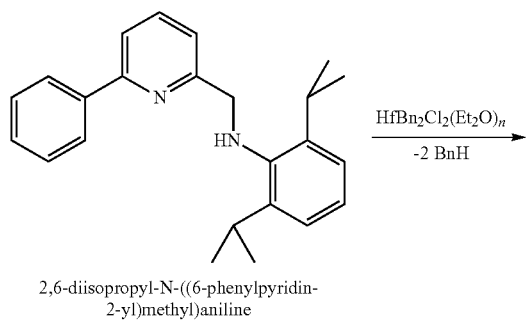

2,6-diisopropyl-N-((6-phenylpyridin-
2-yl)methyl)aniline

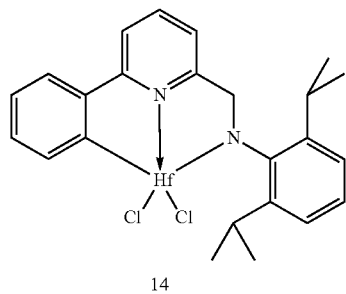

14

Synthesis of 14.

Benzene (10 mL) was added to a combination of 2,6-diisopropyl-N-((6-phenylpyridin-2-yl)methyl)aniline (0.269 g, 0.780 mmol) and HfBn2Cl2(OEt2)1.8 (0.441 g, 0.780 mmol). The orange solution was heated to 70° C. for 105 minutes. The volatiles were then evaporated to near dryness. Additional benzene (5 mL) was then added and the suspended solid was collected on a fritted disk, washed with benzene (3 mL), then hexanes (3 mL), and dried under reduced pressure at 60° C. Yield: 0.407 g, 88.2%. $^1$H NMR (500 MHz, CD$_2$Cl$_2$): δ 8.00 (1H, t), 7.94 (1H, d), 7.81 (2H, d), 7.40-7.15 (6H, m), 5.40 (2H, s), 3.50 (2H, sept), 1.33 (6H, d), 1.17 (6H, d).

Complex R.

Benzene (10 mL) was added to a mixture of complex 14 (0.246 g, 0.415 mmol) and PhCH=NPh (0.0752 g, 0.415 mmol) to form a pale yellow suspension. The mixture was heated to 70° C. for 3 hours followed by almost 2 hours at 80° C. The volatiles were then evaporated under a stream of nitrogen to afford an oil. This was triturated with hexanes (4 mL) to afford a yellow solid that was isolated and dried under reduced pressure at 60° C. Yield: 0.247 g, 69.3%.

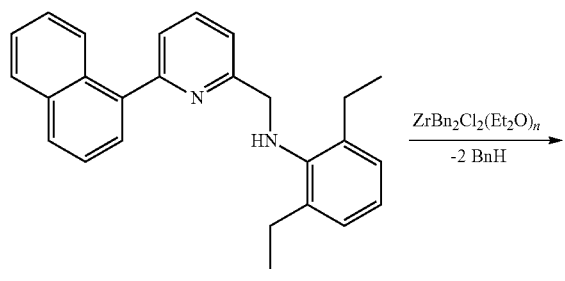

2,6-diethyl-N-((6-(naphthalen-1-
yl)pyridin-2-yl)methyl)aniline

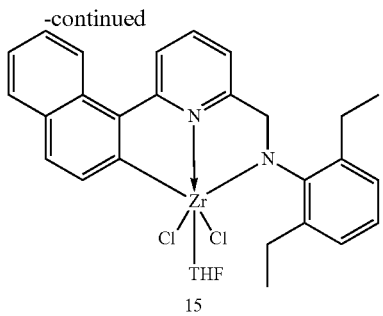

15

Synthesis of 15.

Benzene (15 mL) was added to a combination of 2,6-diethyl-N-((6-(naphthalen-1-yl)pyridin-2-yl)methyl)aniline (0.662 g, 1.81 mmol) and ZrBn$_2$Cl$_2$(OEt$_2$)$_{1.1}$ (0.766 g, 1.81 mmol). The mixture was heated to 60° C. in the dark. After 1 hour the volatiles were evaporated to afford a brown solid that was washed with pentane. The solid was then dissolved in warm THF (15 mL) and filtered. Cooling to −5° C. afforded the product as yellow crystals that were isolated and dried under reduced pressure. Yield: 0.50 g, 40%. NMR spectroscopic data indicated the presence of 2.25 equivalents of THF which is either cocrystallized, coordinated, or both. $^1$H NMR (250 MHz, CD2Cl2): δ 8.53 (1H, d), 8.21 (1H, d), 8.00 (2H, t), 7.87 (1H, d), 7.75 (1H, d), 7.57 (1H, t), 7.45 (1H, t), 7.32 (1H, d), 7.22 (3H, s), 5.24 (2H, s), 3.74 (9H, m), 2.85 (4H, m), 1.75 (9H, m), 1.26 (6H, t).

Complex S.

CH$_2$Cl$_2$ (3 mL) was added to a mixture of complex 15 (0.229 g, 0.332 mmol) and PhCH=NPh (0.07621 g, 0.342 mmol) to form a homogeneous orange-yellow solution. Toluene (4 mL) was then added and the vial was capped and heated to 65° C. After 16 hours the volatiles were evaporated under a stream of nitrogen and toluene (5 mL was added. The mixture was then heated to 110° C. for 1 hour. The volatiles were then evaporated and the residue was crystallized by dissolution in warm toluene (1 mL) followed by the slow addition of Et$_2$O (1 mL). The product was isolated as yellow-orange crystals which were washed with Et$_2$O and dried under reduced pressure. Yield: 0.083 g, 34%.

General Polymerization Procedures

Propylene homopolymerizations were carried out in a parallel, pressure reactor, as generally described in U.S. Pat. No. 6,306,658; U.S. Pat. No. 6,455,316; U.S. Pat. No. 6,489,168; WO 00/09255; and Murphy et al., J. Am. Chem. Soc., 2003, 125, pages 4306-4317, each of which is fully incorporated herein by reference. Although the specific quantities, temperatures, solvents, reactants, reactant ratios, pressures, and other variables are frequently changed from one polymerization run to the next, the following describes a typical polymerization performed in a parallel, pressure reactor.

A pre-weighed glass vial insert and disposable stirring paddle were fitted to each reaction vessel of the reactor, which contains 48 individual reaction vessels. The reactor was then closed and each vessel was individually heated to a set temperature (usually between 50 and 110° C.) and propylene (typically 1 mL) was added as a condensed liquid. Tri-n-octylaluminum in toluene (100 microliters, 10 mM in toluene, 1 micromol) was added to act as a co-catalyst/scavenger followed by enough solvent (typically isohexane) to bring the total reaction volume, including the subsequent additions, to 5 mL.

The contents of the vessel were then stirred at 800 rpm. An activator solution (usually 1.0 molar equivalents of dimethyl anilinium tetrakis-pentafluorophenyl borate dissolved in toluene or 100-1000 molar equivalents of methyl alumoxane (MAO) in toluene) was then injected into the reaction vessel along with 500 microliters of isohexane, followed by a toluene solution of catalyst (typically 0.40 mM in toluene, usually 20-40 nanomols of catalyst) and another aliquot of isohexane (500 microliters). Equivalence is determined based on the mol equivalents relative to the moles of the transition metal in the catalyst complex.

The reaction was then allowed to proceed until a predetermined amount of pressure uptake is observed (10 to 20 psi, (0.07 to 0.14 MPa)). At this point, the reaction was quenched by pressurizing the vessel with compressed air. After the polymerization reaction, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight, and by DSC (see below) to determine melting point.

To determine various molecular weight related values by GPC, high temperature size exclusion chromatography was performed using an automated "Rapid GPC" system as generally described in U.S. Pat. No. 6,491,816; U.S. Pat. No. 6,491,823; U.S. Pat. No. 6,475,391; U.S. Pat. No. 6,461,515; U.S. Pat. No. 6,436,292; U.S. Pat. No. 6,406,632; U.S. Pat. No. 6,175,409; U.S. Pat. No. 6,454,947; U.S. Pat. No. 6,260,407; and U.S. Pat. No. 6,294,388; each of which is fully incorporated herein by reference for US purposes. This apparatus has a series of three 30 cm×7.5 mm linear columns, each containing PLgel 10 um, Mix B. The GPC system was calibrated using polystyrene standards ranging from 580-3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.1-0.9 mg/mL. 250 uL of a polymer solution was injected into the system. The concentration of the polymer in the eluent was monitored using an evaporative light scattering detector. The molecular weights presented are relative to linear polystyrene standards and are uncorrected.

Differential Scanning calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./minutes and then cooled at a rate of 50° C./min. Melting points were collected during the heating period.

The Effect of Substitution at the $R^{17}$ Position on Molecular Weight Distribution With respect to the structures in Table 1, substitution at the $R^{17}$ position is desirable because catalysts with this feature have the unexpected ability to produce polyolefins with bimodal molecular weight distributions. The extent of the bimodality of the polyolefins produced using these systems is expected to depend on process conditions that include temperature, pressure, solvent, etc.

Propylene Polymerizations Using Catalysts F, I, M, R, and S.

The data for these runs is shown in Table 2 below. Catalysts F, I, and M lack substitution at the $R^{17}$ position (see Table 1 for structures) and are presented as comparisons. Catalysts R and S both feature substitution the $R^{17}$ position with a phenyl group. The GPC data for the polypropylene samples produced by catalysts R and S indicate that these catalysts can produce polyolefin products that have GPC traces that indicate the presence of bimodal (or multimodal) molecular weight distribution product. This is most clearly observed in run 9 where the product has a well resolved bimodal molecular weight distribution (FIG. 13). Similarly the polypropylene produced in run 9 has a bimodal molecular weight distribution, but one that is less resolved so that in the GPC trace (FIG. 14) it appears as a high MW shoulder feature. In contrast, catalysts F, I, and M form polyolefin products with GPC traces that lack any features suggestive of bimodal molecular weight distribution.

TABLE 2

Summary of propylene polymerization data. Conditions: isohexane solvent, propylene added = 1 mL, total volume = 5 mL, tri(n-octyl)aluminum = 300 nmol, catalyst = 20 nmol, N,N-dimethylanilinium tetrakis(pentafluorophenyl)borate activator (20 nmol).

Figure 6:
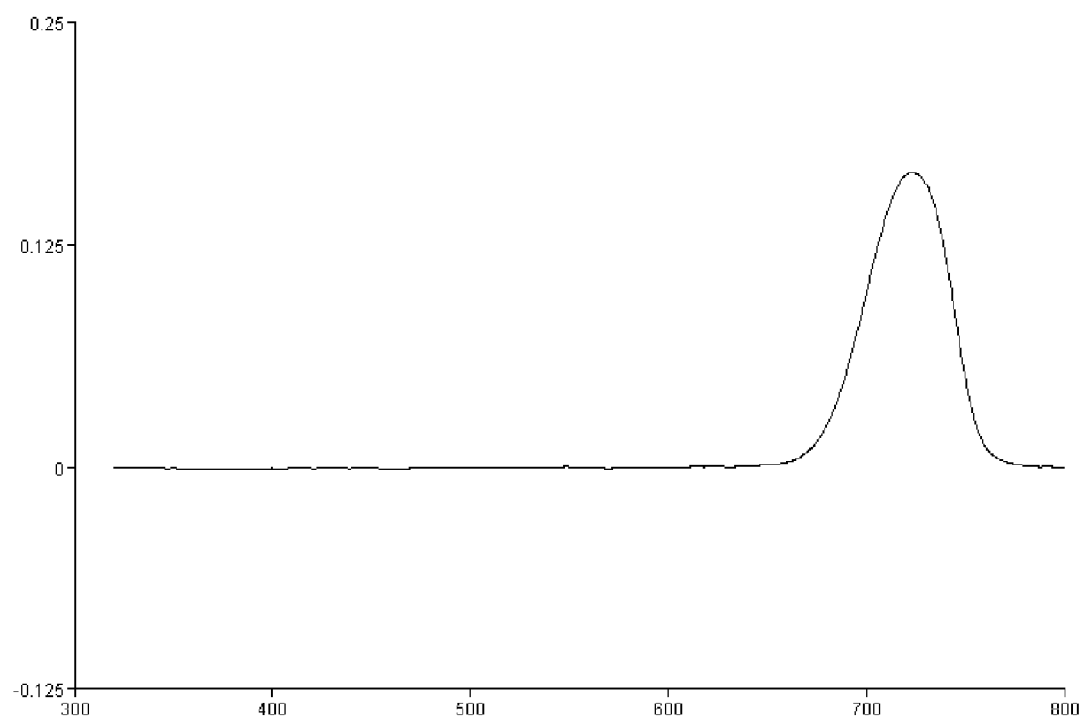
FIG. 6 is a GPC trace for run 1 of Table 2.
Figure 7:
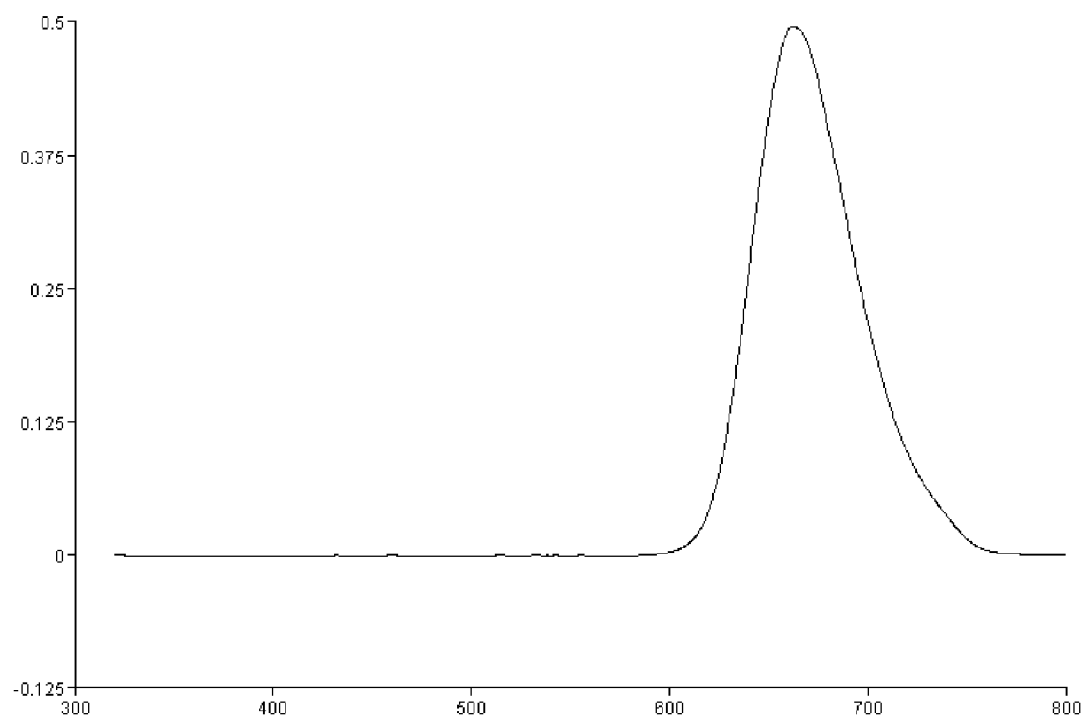
FIG. 7 is a GPC trace for run 2 of Table 2.
Figure 8:
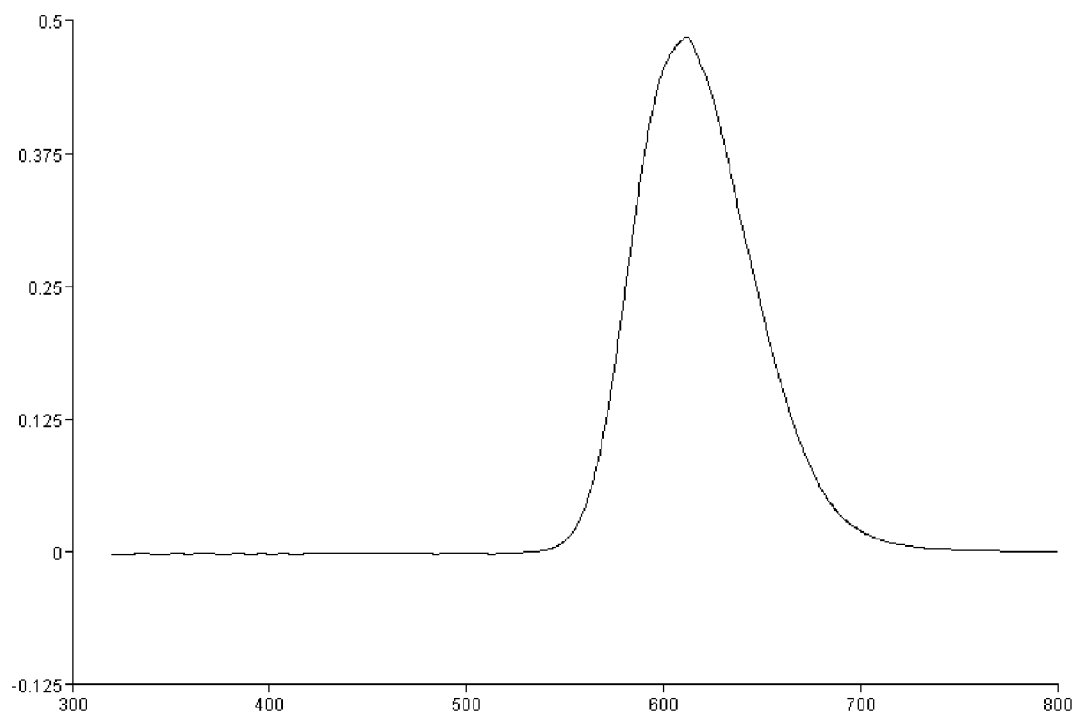
FIG. 8 is a GPC trace for run 3 of Table 2.
Figure 9:
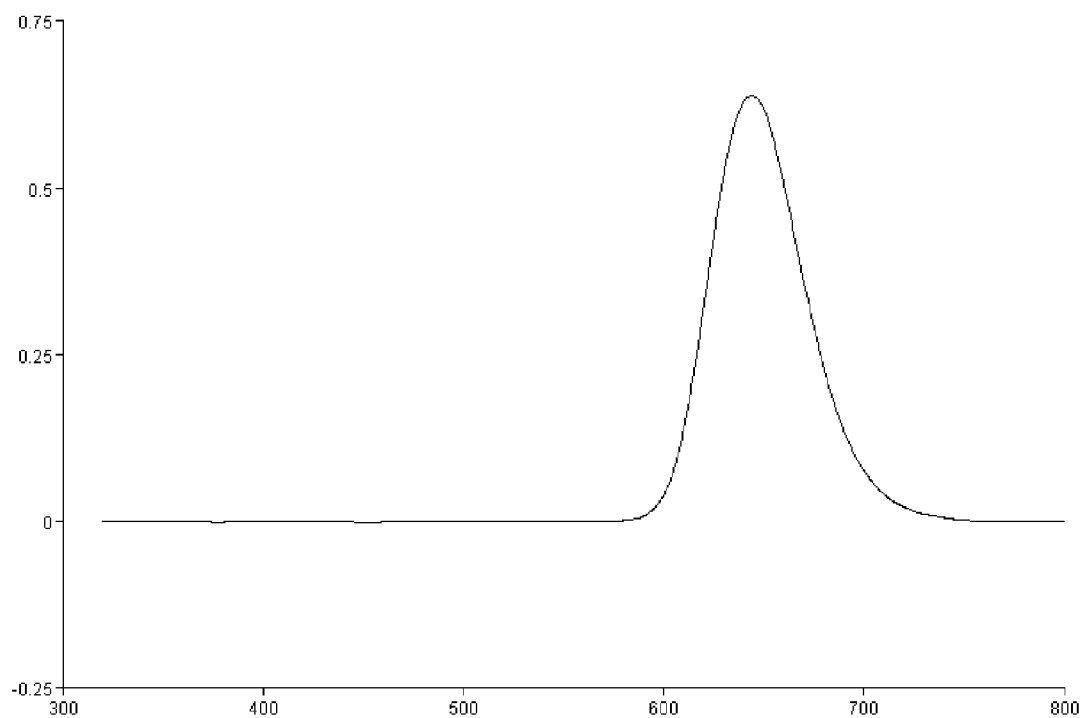
FIG. 9 is a GPC trace for run 4 of Table 2.
Figure 10:
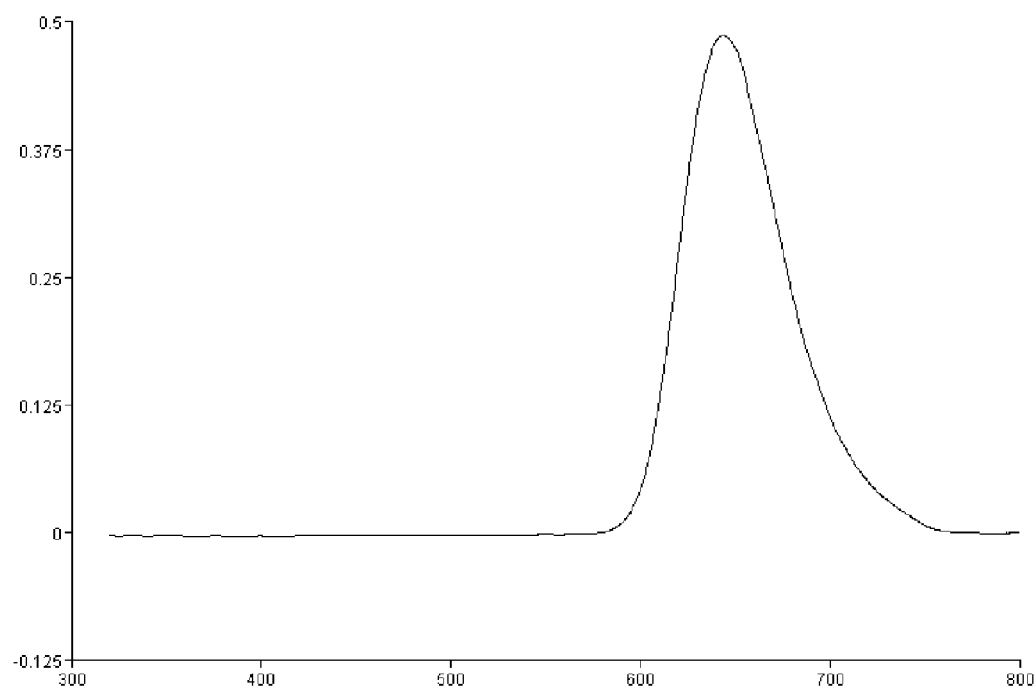
FIG. 10 is a GPC trace for run 5 of Table 2.
Figure 11:
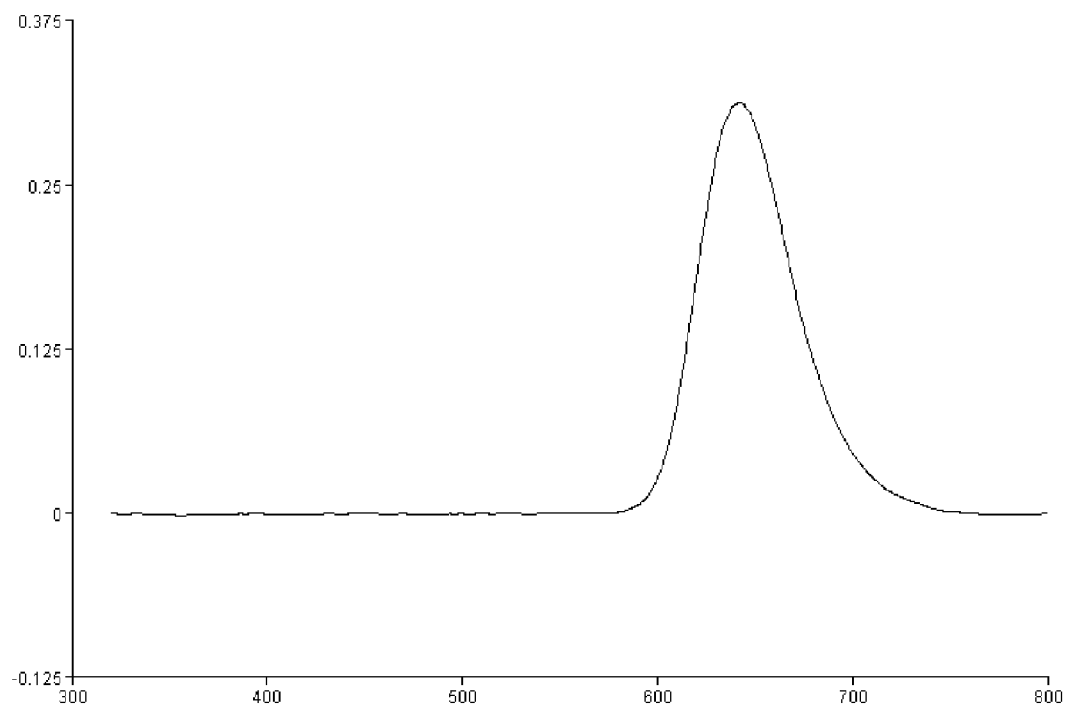
FIG. 11 is a GPC trace for run 6 of Table 2.
Figure 12:
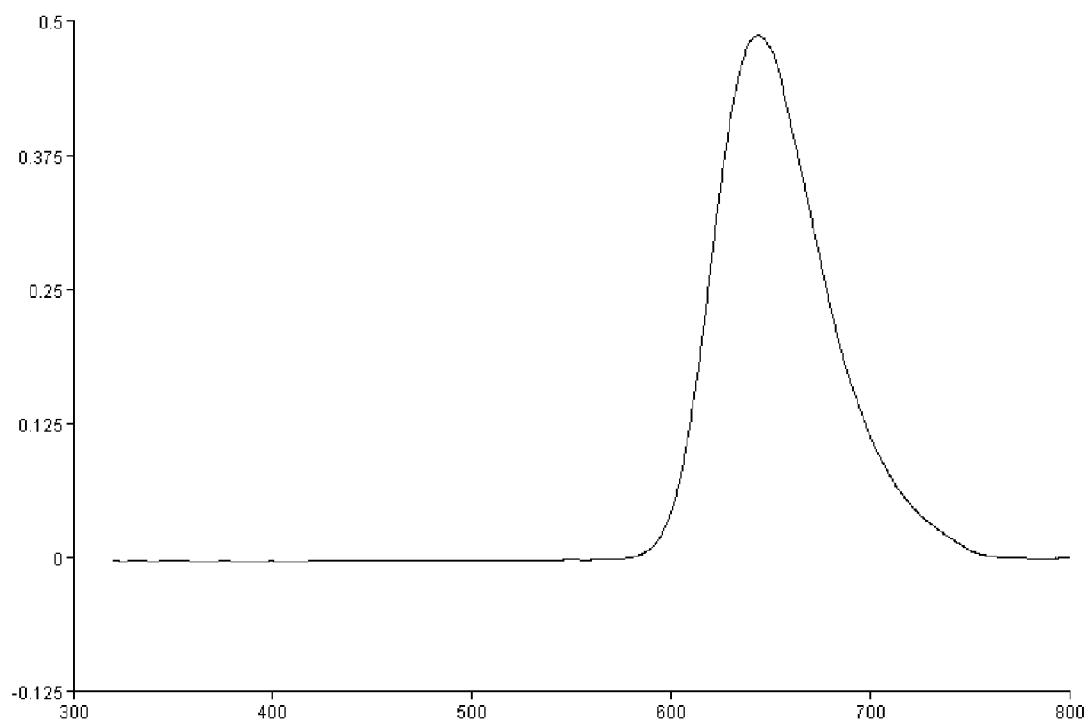
FIG. 12 is a GPC trace for run 7 of Table 2.
Figure 15:
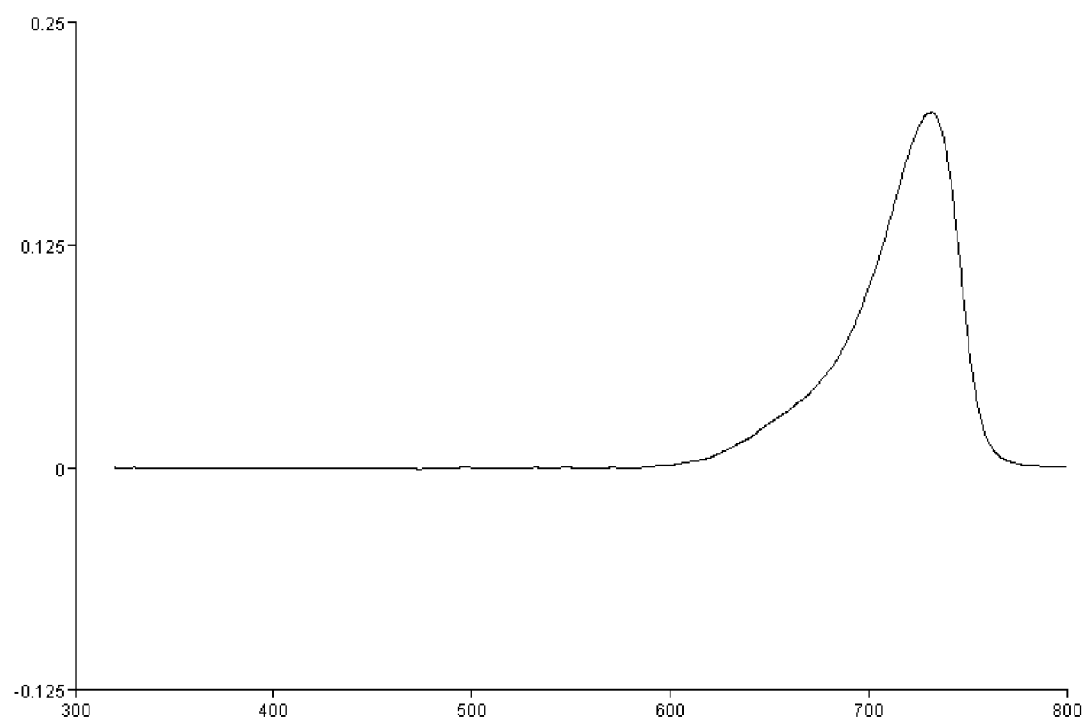
FIG. 15 is a GPC trace for run 10 of Table 2.
Figure 16:
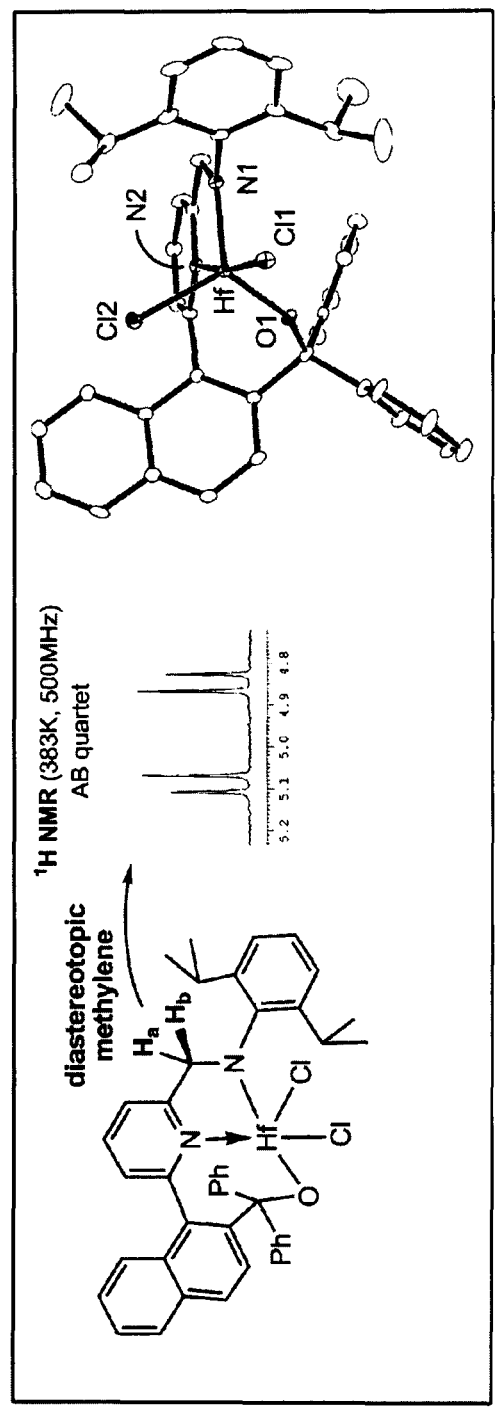
FIG. 16 is a proton NMR illustrating a diastereotopic methylene in a pyridyl amide catalyst composition.

| run | catalyst | T (° C.) | Act.* | GPC trace description | Mw | Mn | Mw/Mn | Tm (° C.) |
|---|---|---|---|---|---|---|---|---|
| 1 | F | 70 | 310 | narrow (FIG. 6) | 3,880 | 2,823 | 1.4 | n.d. |
| 2 | F | 100 | 8742 | narrow (FIG. 7) | 18,473 | 9,782 | 1.9 | 96.0 |
| 3 | I | 70 | 1,619 | narrow (FIG. 8) | 100,492 | 46,748 | 2.1 | 138.6 |
| 4 | I | 100 | 3,342 | narrow (FIG. 9) | 34,578 | 20,479 | 1.7 | 127.0 |
| 5 | M | 70 | 989 | narrow (FIG. 10) | 107,657 | 60,630 | 1.8 | 136.3 |
| 6 | M | 100 | 357 | narrow (FIG. 11) | 35,816 | 20,310 | 1.8 | 130.1 |
| 7 | R | 70 | 10,710 | narrow (FIG. 12) | 32,698 | 15,413 | 2.1 | n.d. |
| 8 | R | 100 | 3,396 | bimodal (FIG. 13) | 52,887 | 6,000 | 8.8 | n.d. |
| 9 | S | 70 | 1,069 | high MW shoulder (FIG. 14) | 20,319 | 4,985 | 4.1 | n.d. |
| 10 | S | 100 | 385 | high MW tail (FIG. 15) | 5,589 | 2,938 | 1.9 | n.d. |

*Activity given as g polymer/mmol catalyst/hour.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise, whenever a composition, an element, or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

What is claimed is:

1. A pyridyldiamido transition metal complex having the general formula (A) or (B):

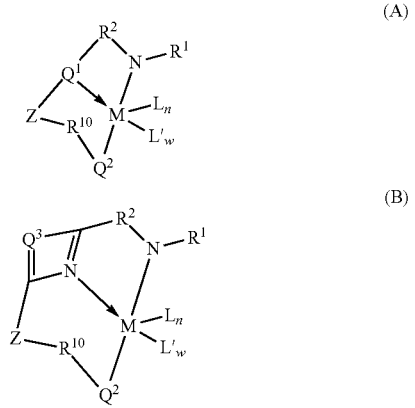

wherein:

M is a Group 3, 4, 5, 6, 7, 8, 9, 10, 11, or 12 metal;

$Q^1$ is a group that links $R^2$ and Z by a three atom bridge with the central of the three atoms being a group 15 or 16 element represented by the formula: $-G^1-G^2-G^3-$ where $G^2$ is a group 15 or 16 atom, $G^1$ and $G^3$ are each a group 14, 15 or 16 atom, where $G^1$, $G^2$, and $G^3$, or $G^1$ and $G^2$, or $G^1$ and $G^3$, or $G^2$ and $G^3$ may form a singular or multi ring system, and if any of $G^1$ and/or $G^3$ is a group 14 atom then $R^{30}$ and $R^{31}$ are bound to such G atom(s), and if any of $G^1$, $G^2$, and/or $G^3$ is a group 15 atom then $R^{30}$ is bound to such G atom(s), where each $R^{30}$ and $R^{31}$ is, independently, hydrogen or a $C_1$ to $C_{100}$ hydrocarbyl group;

$Q^2$ is a group that forms an anionic bond with M, said $Q^2$ group being selected from O, S, Se, Te, Po, $NR^{17}$ or $PR^{17}$, where $R^{17}$ is selected from hydrogen, hydrocarbyls, substituted hydrocarbyls, alkoxy, aryloxy, halogen, amino, and silyl;

$Q^3$ is -(TT)- or -(TTT)-, where each T is carbon or a heteroatom and said carbon or heteroatom may be unsubstituted or substituted with one or more $R^{30}$ groups that together with the "—C-$Q^3$=C—" fragment, forms a 5- or 6-membered cyclic group or a polycyclic group including the 5- or 6-membered cyclic group, where each $R^{30}$ group is, independently, hydrogen or a $C_1$ to $C_{100}$ hydrocarbyl group;

$R^1$ is selected from the group consisting of hydrocarbyls, and substituted hydrocarbyls, or silyl groups;

$R^2$ and $R^{10}$ are each, independently, -E($R^{12}$)($R^{13}$)— with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

Z is $-(R_{14})_pC-C(R_{15})_q-$, where $R_{14}$ and $R_{15}$ are independently selected from the group consisting of hydrogen, hydrocarbyls, and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings;

p is 1 or 2;

q is 1 or 2;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3, or 4; and wherein n+w is no greater than 4;

provided that one of $R^2$ and $R^{10}$ is asymmetrically substituted and the other is symmetrically substituted.

2. A pyridyldiamido transition metal complex represented by the formula (I) or (II):

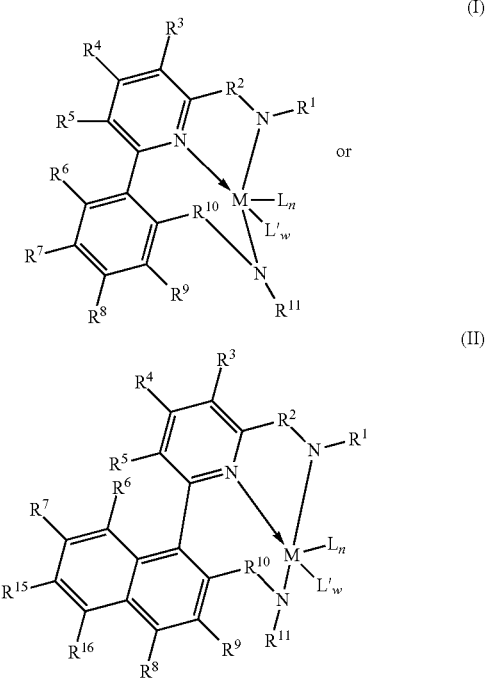

wherein:

M is a Group 3, 4, 5, 6, 7, 8, 9, 10, 11, or 12 metal;

$R^1$ and $R^{11}$ are independently selected from the group consisting of hydrocarbyls, and substituted hydrocarbyls, or silyl groups;

$R^2$ and $R^{10}$ are each, independently, -E($R^{12}$)($R^{13}$)— with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

$R^3$, $R^4$, and $R^5$ are independently selected from the group consisting of hydrogen, hydrocarbyls, substituted hydrocarbyls, alkoxy, aryloxy, halogen, amino, and silyl, and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^6$, $R^7$, $R^8$, $R^9$, $R^{15}$, and $R^{16}$ are independently selected from the group consisting of hydrogen, hydrocarbyls, substituted hydrocarbyls, alkoxy, halogen, amino, and silyl, and wherein adjacent R groups ($R^6$ & $R^7$, and/or $R^7$ & $R^{15}$, and/or $R^{16}$ & $R^{15}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3, or 4; and wherein n+w is no greater than 4;

provided that one of $R^2$ and $R^{10}$ is asymmetrically substituted and the other is symmetrically substituted.

3. The complex of claim 1 or 2, wherein M is Ti, Zr, or Hf.

4. The complex of claim 1 or 2, wherein $R^2$ is represented by the formula:

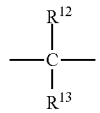

where $R^{12}$ is hydrogen, alkyl, aryl, or halogen; and $R^{13}$ is hydrogen, alkyl, aryl, or halogen.

5. The complex of claim 2, wherein $R^6$, $R^7$, $R^8$, $R^9$, $R^{15}$, and $R^{16}$, are independently selected from the group consisting of hydrogen, hydrocarbyls, substituted hydrocarbyls, alkoxy, halogen, amino, and silyl.

6. The complex of claim 2, wherein $R^1$, $R^3$, $R^4$, $R^5$, $R^{11}$ each contain from 1 to 30 carbon atoms.

7. The complex of claim 2, wherein E is carbon and $R^1$ and $R^{11}$ are independently selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyls groups with from one to ten carbons.

8. The complex of claim 1 or 2, wherein each L is independently selected from the group consisting of halide, alkyl, aryl, alkoxy, amido, hydrido, phenoxy, hydroxy, silyl, allyl, alkenyl, and alkynyl.

9. The complex of claim 1 or 2, wherein each L' is independently selected from the group consisting of ethers, thioethers, amines, nitriles, imines, pyridines, and phosphines.

10. The complex of claim 1 or 2, wherein for $R^{10}$, E is carbon, $R^{12}$ is phenyl, and $R^{13}$ is H.

11. The complex of claim 1 or 2, wherein the $R^2$ group(s) are selected from the group consisting of $CH_2$, $CMe_2$, $SiMe_2$, $SiEt_2$, $SiPr_2$, $SiBu_2$, $SiPh_2$, $Si(aryl)_2$, and $Si(alkyl)_2$, CH(aryl), CH(Ph), CH(alkyl), CH(2-isopropylphenyl), where alkyl is a $C_1$ to $C_{40}$ alkyl group, aryl is a $C_5$ to $C_{40}$ aryl group.

12. The complex of claim 1 or 2, wherein the $R^{10}$ group(s) are selected from the group consisting of $CH_2$, $CMe_2$, $SiMe_2$, $SiEt_2$, $SiPr_2$, $SiBu_2$, $SiPh_2$, $Si(aryl)_2$, and $Si(alkyl)_2$, CH(aryl), CH(Ph), CH(alkyl), CH(2-isopropylphenyl), where alkyl is a $C_1$ to $C_{40}$ alkyl group, aryl is a $C_5$ to $C_{40}$ aryl group, and Ph is phenyl.

13. The complex of claim 1 or 2, wherein $R^2$ is one or more of $CH_2$ and $CMe_2$, and $R^{10}$ is one or more of CH(Ph), CH(aryl), and CH(alkyl), where alkyl is a $C_1$ to $C_{40}$ alkyl group, aryl is a $C_5$ to $C_{40}$ aryl group, and Ph is phenyl.

14. The complex of claim 1 or 2, wherein $R^2$ and $R^{10}$ groups (expressed as $R^2$ & $R^{10}$ are: ($CH_2$ & CH(Ph)), ($CMe_2$ and CH(Ph)), ($CH_2$ and CH(aryl)), ($CH_2$ and CH(alkyl)), where alkyl is a $C_1$ to $C_{40}$ alkyl group, aryl is a $C_5$ to $C_{40}$ aryl group and Ph is phenyl.

15. A catalyst system comprising an activator and a pyridyldiamido transition metal complex represented by the formula (A) or (B):

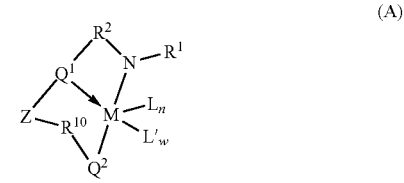

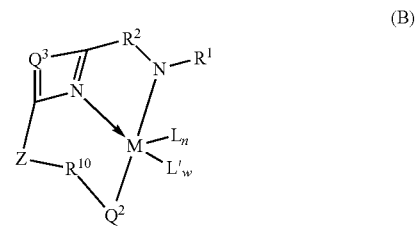

wherein:

M is a Group 3, 4, 5, 6, 7, 8, 9, 10, 11, or 12 metal;

$Q^1$ is a group that links $R^2$ and Z by a three atom bridge with the central of the three atoms being a group 15 or 16 element represented by the formula: -$G^1$-$G^2$-$G^3$- where $G^2$ is a group 15 or 16 atom, $G^1$ and $G^3$ are each a group 14, 15 or 16 atom, where $G^1$, $G^2$, and $G^3$, or $G^1$ and $G^2$, or $G^1$ and $G^3$, or $G^2$ and $G^3$ may form a singular or multi ring system, and if any of $G^1$ and/or $G^3$ is a group 14 atom then $R^{30}$ and $R^{31}$ are bound to such G atom(s), and if any of $G^1$, $G^2$, and/or $G^3$ is a group 15 atom then $R^{30}$ is bound to such G atom(s), where each $R^{30}$ and $R^{31}$ is, independently, hydrogen or a $C_1$ to $C_{100}$ hydrocarbyl group;

$Q^2$ is a group that forms an anionic bond with M, said $Q^2$ group being selected from O, S, Se, Te, Po, $NR^{17}$ or $PR^{17}$, where $R^{17}$ is selected from hydrogen, hydrocarbyls, substituted hydrocarbyls, alkoxy, aryloxy, halogen, amino, and silyl;

Q³ is -(TT)- or -(TTT)-, where each T is carbon or a heteroatom and said carbon or heteroatom may be unsubstituted or substituted with one or more $R^{30}$ groups that together with the "—C-Q³=C—" fragment, forms a 5- or 6-membered cyclic group or a polycyclic group including the 5- or 6-membered cyclic group, where each $R^{30}$ group is, independently, hydrogen or a $C_1$ to $C_{100}$ hydrocarbyl group;

$R^1$ is selected from the group consisting of hydrocarbyls, and substituted hydrocarbyls, or silyl groups;

$R^2$ and $R^{10}$ are each, independently, -E($R^{12}$)($R^{13}$)— with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

Z is —($R_{14}$)$_p$C—C($R_{15}$)$_q$—, where $R_{14}$ and $R_{15}$ are independently selected from the group consisting of hydrogen, hydrocarbyls, and substituted hydrocarbyls, and wherein adjacent $R_{14}$ and $R_{15}$ groups may be joined to form an aromatic or saturated, substituted or unsubstituted hydrocarbyl ring, where the ring has 5, 6, 7, or 8 ring carbon atoms and where substitutions on the ring can join to form additional rings;

p is 1 or 2;

q is 1 or 2;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3, or 4; and wherein n+w is no greater than 4;

provided that one of $R^2$ and $R^{10}$ is asymmetrically substituted and the other is symmetrically substituted.

16. A catalyst system comprising an activator and a pyridyldiamido transition metal complex represented by the formula (I) or (II):

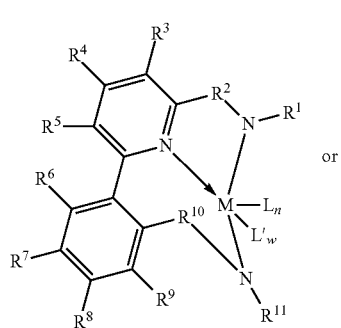

(I)

or

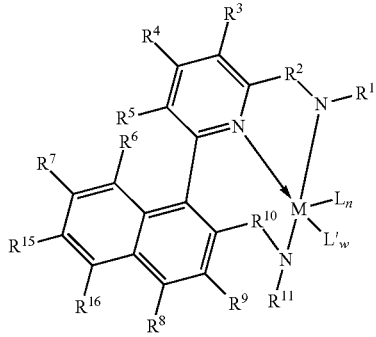

(II)

wherein:

M is a Group 3, 4, 5, 6, 7, 8, 9, 10, 11, or 12 metal;

$R^1$ and $R^{11}$ are independently selected from the group consisting of hydrocarbyls, and substituted hydrocarbyls, or silyl groups;

$R^2$ and $R^{10}$ are each, independently, -E($R^{12}$)($R^{13}$)— with E being carbon, silicon, or germanium, and each $R^{12}$ and $R^{13}$ being independently selected from the group consisting of hydrogen, hydrocarbyls, and substituted hydrocarbyls, alkoxy, silyl, amino, aryloxy, halogen, and phosphino, $R^{12}$ and $R^{13}$ may be joined to form a saturated, substituted or unsubstituted hydrocarbyl ring, where the ring has 4, 5, 6, or 7 ring carbon atoms and where substitutions on the ring can join to form additional rings, or $R^{12}$ and $R^{13}$ may be joined to form a saturated heterocyclic ring, or a saturated substituted heterocyclic ring where substitutions on the ring can join to form additional rings;

$R^3$, $R^4$, and $R^5$ are independently selected from the group consisting of hydrogen, hydrocarbyls, substituted hydrocarbyls, alkoxy, aryloxy, halogen, amino, and silyl, and wherein adjacent R groups ($R^3$ & $R^4$ and/or $R^4$ & $R^5$) may be joined to form a substituted or unsubstituted hydrocarbyl or heterocyclic ring, where the ring has 5, 6, 7, or 8 ring atoms and where substitutions on the ring can join to form additional rings;

$R^6$, $R^7$, $R^8$, $R^9$, $R^{15}$, and $R^{16}$ are independently selected from the group consisting of hydrogen, hydrocarbyls, substituted hydrocarbyls, alkoxy, halogen, amino, and silyl, and wherein adjacent R groups ($R^6$ & $R^7$, and/or $R^7$ & $R^{15}$, and/or $R^{16}$ & $R^{15}$, and/or $R^8$ & $R^9$) may be joined to form a saturated, substituted or unsubstituted hydrocarbyl or heterocyclic ring, where the ring has 5, 6, 7, or 8 ring carbon atoms and where substitutions on the ring can join to form additional rings;

L is an anionic leaving group, where the L groups may be the same or different and any two L groups may be linked to form a dianionic leaving group;

n is 0, 1, 2, 3, or 4;

L' is neutral Lewis base;

w is 0, 1, 2, 3 or 4; and wherein n+w is no greater than 4;

provided that one of $R^2$ and $R^{10}$ is asymmetrically substituted and the other is symmetrically substituted.

17. The catalyst system of claim 15 or 16, wherein the activator is an alumoxane.

18. The catalyst system of claim 15 or 16, wherein the activator is a non-coordinating anion.

19. The catalyst system of claim 15 or 16, wherein the $R^2$ group(s) are selected from the group consisting of $CH_2$, $CMe_2$, $SiMe_2$, $SiEt_2$, $SiPr_2$, $SiBu_2$, $SiPh_2$, $Si(aryl)_2$, and Si(alkyl)$_2$, CH(aryl), CH(Ph), CH(alkyl), CH(2-isopropylphenyl), and the R$^{10}$ group(s) are selected from the group consisting of CH$_2$, CMe$_2$, SiMe$_2$, SiEt$_2$, SiPr$_2$, SiBu$_2$, SiPh$_2$, Si(aryl)$_2$, and Si(alkyl)$_2$, CH(aryl), CH(Ph), CH(alkyl), CH(2-isopropylphenyl), where alkyl is a C$_1$ to C$_{40}$ alkyl group, aryl is a C$_5$ to C$_{40}$ aryl group, and Ph is phenyl.

20. A polymerization process to produce multimodal polyolefin comprising:
   a) contacting one or more olefin monomers with the catalyst system of claim 15 or 16; and
   b) obtaining multimodal olefin polymer.

21. The process of claim 20, wherein the activator is an alumoxane.

22. The process of claim 20, wherein the activator is a non-coordinating anion.

23. The process of claim 20, wherein the monomer comprises ethylene.

24. The process of claim 20, wherein the monomer comprises propylene.

25. The process of claim 20, wherein the pyridyldiamido transition metal complex is supported.

26. The pyridyldiamido transition metal complex of claim 1, wherein T is C, O, S, or N.

27. The catalyst system of claim 15, wherein T is C, O, S, or N.

28. A polymerization process comprising: a) contacting one or more olefin monomers with the catalyst system of claim 15 or 16; and b) obtaining multimodal olefin polymer, wherein the activator is a non-coordinating anion, and the monomer comprises ethylene and propylene.

29. A polymerization process comprising: a) contacting one or more olefin monomers with the catalyst system of claim 15 or 16; and b) obtaining multimodal olefin polymer, wherein the activator is a non-coordinating anion, the monomer comprises ethylene and propylene, and the pyridyldiamido transition metal complex is supported.

* * * * *